(12) United States Patent
Waite et al.

(10) Patent No.: US 11,143,887 B2
(45) Date of Patent: *Oct. 12, 2021

(54) FLUIDIC MODULE FOR ACCOMMODATING SOFT CONTACT LENS

(71) Applicant: OneFocus Vision, Inc., Fernandina Beach, FL (US)

(72) Inventors: Steven B. Waite, Fernandina Beach, FL (US); Amitava Gupta, Roanoke, VA (US); Urban Schnell, Liebefeld-Bern (CH); Jean-Christophe Roulet, Liebefeld-Bern (CH); Michel Saint-Ghislain, Liebefeld-Bern (CH); Stefan Troller, Liebefeld-Bern (CH)

(73) Assignee: OneFocus Vision, Inc., Fernandina Beach, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/385,623

(22) Filed: Apr. 16, 2019

(65) Prior Publication Data

US 2019/0361269 A1    Nov. 28, 2019

Related U.S. Application Data

(63) Continuation of application No. 15/186,024, filed on Jun. 17, 2016, now Pat. No. 10,302,968, which is a
(Continued)

(51) Int. Cl.
*G02C 7/04* (2006.01)
*G02C 7/08* (2006.01)
(Continued)

(52) U.S. Cl.
CPC ............ *G02C 7/085* (2013.01); *A61F 9/0017* (2013.01); *B29D 11/00028* (2013.01);
(Continued)

(58) Field of Classification Search
CPC .......... G02C 7/04; G02C 7/049; G02C 7/022; G02C 7/085
(Continued)

(56) References Cited

U.S. PATENT DOCUMENTS 3,246,941 A     4/1966 Moss
3,594,074 A     7/1971 Rosen
(Continued)

FOREIGN PATENT DOCUMENTS

CN    101277659 A    10/2008
CN    101351169 A    1/2009
(Continued)

OTHER PUBLICATIONS

European Search Report and Opinion for European Application No. 14743938.4 (dated Sep. 2, 2016).
(Continued)

*Primary Examiner* — Darryl J Collins
(74) *Attorney, Agent, or Firm* — FisherBroyles, LLP; John Shimmick

(57) ABSTRACT

A meniscus shaped lens module comprises one or more structures that decrease an amount of pressure or force to move one or more surfaces of the lens module and increase a separation distance of anterior and posterior surfaces of the module in order to provide an increase in optical power. A lens structure of the module comprises one or more of a pattern of a surface of a central chamber, a meniscus, a reduced diameter or a soft material in order to provide increased amounts of curvature of an outer contact lens surface with decreased amounts of pressure. The pattern can be formed in one or more of many ways, and may comprise one or more of folds, patterning, bellows or concertinaed
(Continued)

surface of an optically transmissive material having a substantially uniform thickness such as a sheet of a membrane material.

17 Claims, 28 Drawing Sheets

Related U.S. Application Data continuation of application No. PCT/US2014/071988, filed on Dec. 22, 2014.

(60) Provisional application No. 62/031,290, filed on Jul. 31, 2014, provisional application No. 61/919,691, filed on Dec. 20, 2013.

(51) Int. Cl.
  *A61F 9/00* (2006.01)
  *B29D 11/00* (2006.01)
  *G02B 3/14* (2006.01)

(52) U.S. Cl.
  CPC .. *B29D 11/00048* (2013.01); *B29D 11/00134* (2013.01); *G02B 3/14* (2013.01); *G02C 7/04* (2013.01); *G02C 7/049* (2013.01); *G02C 7/083* (2013.01); *B29K 2825/06* (2013.01); *G02C 7/048* (2013.01); *G02C 2202/18* (2013.01)

(58) Field of Classification Search
  USPC .......................................... 351/159.34, 159.68
  See application file for complete search history.

(56) References Cited

U.S. PATENT DOCUMENTS

| | | | |
|---|---|---|---|
| 4,174,156 A | 11/1979 | Glorieux | |
| 4,477,158 A | 10/1984 | Pollock | |
| 4,477,458 A | 10/1984 | Mora | |
| 4,512,040 A | 4/1985 | McClure | |
| 4,525,044 A | 6/1985 | Bauman | |
| 5,684,637 A | 11/1997 | Floyd | |
| 5,760,871 A | 6/1998 | Kosoburd | |
| 6,054,075 A | 4/2000 | Inaba | |
| 6,092,899 A | 7/2000 | Wanders | |
| 6,288,846 B1 | 9/2001 | Stoner, Jr. | |
| 7,261,736 B1 | 8/2007 | Azar | |
| 7,322,695 B2 | 1/2008 | Wooley | |
| 7,452,075 B2 | 11/2008 | Iuliano | |
| 7,503,652 B2 | 3/2009 | Menezes | |
| 7,517,084 B2 | 4/2009 | Wooley | |
| 7,559,650 B2 | 7/2009 | Iuliano | |
| 7,694,464 B2 | 4/2010 | Garcia | |
| 7,699,462 B2 | 4/2010 | Godoy | |
| 7,810,925 B2 | 10/2010 | Evans | |
| 7,959,284 B2 | 6/2011 | Lai | |
| 8,136,942 B2 * | 3/2012 | Gupta | G02B 3/06 351/159.01 |
| 9,910,296 B2 | 3/2018 | Harant | |
| 10,302,968 B2 | 5/2019 | Waite | |
| 2002/0021409 A1 | 2/2002 | Marmo | |
| 2003/0185662 A1 | 10/2003 | Appleton | |
| 2007/0035050 A1 | 2/2007 | Rogers | |
| 2008/0231799 A1 | 9/2008 | Iuliano | |
| 2008/0231801 A1 | 9/2008 | Iuliano | |
| 2010/0039709 A1 | 2/2010 | Lo | |
| 2010/0201009 A1 | 8/2010 | Bruce | |
| 2011/0085131 A1 | 4/2011 | Gupta | |
| 2011/0085243 A1 | 4/2011 | Gupta | |
| 2012/0026597 A1 | 2/2012 | Pugh | |
| 2012/0138488 A1 | 6/2012 | English | |
| 2012/0206691 A1 | 8/2012 | Iwai | |
| 2012/0268712 A1 | 10/2012 | Egan | |
| 2013/0194540 A1 | 8/2013 | Pugh | |
| 2013/0242255 A1 | 9/2013 | Caldarise | |
| 2013/0258277 A1 | 10/2013 | Pugh | |
| 2014/0232982 A1 | 8/2014 | Iwai | |
| 2015/0370093 A1 | 12/2015 | Waite | |
| 2016/0004098 A1 | 1/2016 | Waite | |
| 2016/0018671 A1 | 1/2016 | Waite | |
| 2017/0131570 A1 | 5/2017 | Thompson | |
| 2017/0131571 A1 | 5/2017 | Waite | |
| 2018/0173010 A1 | 6/2018 | Harant | |
| 2019/0048180 A1 | 2/2019 | Harant | |
| 2019/0064546 A1 | 2/2019 | Waite | |

FOREIGN PATENT DOCUMENTS

| | | |
|---|---|---|
| EP | 0605841 A1 | 7/1994 |
| JP | H08187793 A | 7/1996 |
| WO | 9110154 A1 | 7/1991 |
| WO | 2008115251 A1 | 9/2008 |
| WO | 2012051167 A1 | 4/2012 |
| WO | 2012061411 A1 | 5/2012 |
| WO | 2013109315 A2 | 7/2013 |
| WO | 2014117173 A2 | 7/2014 |
| WO | 2014120928 A2 | 8/2014 |
| WO | 2014161002 A2 | 10/2014 |
| WO | 2015095891 A1 | 6/2015 |
| WO | 2016019346 | 2/2016 |
| WO | 2016019351 | 2/2016 |
| WO | 2016019359 | 2/2016 |
| WO | 2017083770 | 5/2017 |
| WO | 2017083771 | 5/2017 |
| WO | 2017083774 | 5/2017 |
| WO | 2018089699 | 5/2018 |

OTHER PUBLICATIONS

European Search Report for European Application No. 14746249.3 (dated Sep. 2, 2016).
European search report with written opinion dated Jul. 24, 2017 for EP Application No. 14872828.
Gulsen; et al., Ophthalmic Drug Delivery through Contact Lenses. Investigative Ophthalmology & Visual Science, Jul. 2004. 45:7; 2342-2347.
Hsu, et al., "Review of Ophthalmic Drug Delivery by Contact Lenses," J. Drug Del. Sci. Tech. 24(2):123-135 (2014).
International Preliminary Report on Patentability for International Application No. PCT/US2014/013427 (dated Aug. 6, 2016).
International Preliminary Report on Patentability for International Application No. PCT/US2014/013859 (dated Aug. 4, 2015).
International Search Report and Written Opinion for International Application No. PCT/US2014/013427 (dated Aug. 20, 2014).
International Search Report and Written Opinion for International Application No. PCT/US2014/013859 (dated Jul, 17, 2014).
International search report with written opinion dated Jun. 2, 2015 for PCT/US2014/071988.
Kim, et al., Diamond Nanogel-Ernbedded Contact Lenses Mediate Lysozyme-Dependent Therapeutic Release. ACSNANO. 2014. 8:3; 2998-3005.
Yuan, et al., Ocular Drug Delivery Nanowafer with Enhanced Therapeutic Efficacy. ACSNANO. 2015. 9:2; 1749-1758.

* cited by examiner

*Fluidic resistance*

$\mu_{liquid}$ : Dynamic viscosity
L: Channel length
w: Channel width
d: Channel depth

Fluidic resistance of rectangular channel ($\lambda$>4.45) by Navier-Stokes $$K_{cap} = \frac{12 \cdot \mu_{liquid} \cdot L}{w \cdot d^3}$$

*Flow rate*

Volume flow rate $Q_v = \Delta P / K_{cap}$

*Numerical application*

$\mu_{M3}$: 3 mPa·s
L: 1 mm   w: 800 µm   d: 10 µm
$\Delta P$: 500 Pa
$\Delta V$: 50 nl (volume of fluid needed to reach 2D in a Ø3 mm central reservoir)

Figure 12A

| Pressure for 2 GPa PVDF [Pa] | Pressure for 3 GPa PVDF [Pa] | Max sag [um] | Volume [nl] | Ø 3.0mm lens Requires 50 [nl] @ 2D | Ø 3.5mm lens Requires 120 [nl] @ 2D |
|---|---|---|---|---|---|
| 500 | 750 | 3.5 | 48 | critical | insufficient |
| 1000 | 1500 | 7 | 96 | ok | insufficient |
| 1250 | 1875 | 8.8 | 120 | ok | critical |
| 1500 | 2250 | 310.5 | 3144 | ok | ok |

☐ Pattern A "smooth surface"
— Results:
  ☐ 6.1 μm sag
  ☐ Volume ~15 nl

☐ Pattern B " best fit"
— Results:
  ☐ 6
  ☐ V

Module specifications

- Central reservoir: 3.0 mm diameter, inside edge
- Length of channel: 1.0 mm
- Geometry of channel: 800 microns X 15 microns (depth)
- Thickness of anterior membrane: 5 microns
- Thickness of posterior membrane: 25 microns
- Total thickness of module: 35-45 microns (including fluid depth of 10-25 microns).

Figure 22B

- ACL anterior surface Optimization
  - 2.5D => reading plane at 400mm in front of eye
  - Optimization on curvature radius and conic constant

- Results
  - Surface equation $$z = \frac{cr^2}{1 + \sqrt{1 - (1+k)\, c^2 r^2}}$$
    - $c = \dfrac{2}{7.461096 \text{ mm}}$
    - $k = -0.393499$
  - MTF @ 100lp/mm = 0.66 (diffraction limited)
  - Sag increase: +8 um (at vertex)

FLUIDIC MODULE FOR ACCOMMODATING SOFT CONTACT LENS

RELATED APPLICATIONS

The present application is a continuation of U.S. application Ser. No. 15/186,024, filed Jun. 17, 2016, now U.S. Pat. No. 10,302,968, issued May 28, 2019, which is a continuation of International Application No. PCT/US2014/071988, filed Dec. 22, 2014, which claims priority to U.S. Provisional Application No. 61/919,691, filed Dec. 20, 2013, and claims priority to U.S. Provisional Application No. 62/031,290 filed on Jul. 31, 2014, the entire disclosures of which are incorporated herein by reference.

This subject matter of the present application is related to the following patent applications: International Application No. PCT/US2014/013427, filed Jan. 28, 2014, U.S. Provisional Application No. 61/757,457, filed Jan. 28, 2013, International Application No. PCT/US2014/013859, filed Jan. 30, 2014, U.S. Provisional Application No. 61/758,416, filed Jan. 30, 2013, U.S. Provisional Application No. 61/857,462, filed Jul. 23, 2013, U.S. Provisional Application No. 62/031,305, filed Jul. 31, 2014, and U.S. Provisional Application No. 62/031,324, filed Jul. 31, 2014, the entire disclosures of which are incorporated herein by reference.

BACKGROUND

Prior treatments of presbyopia include bifocal spectacles, progressive addition lenses, and multifocal contact lenses, as well as reading glasses. The prior approaches can have the disadvantage of not providing focusing power that is dynamic and controllable by the user.

Although it has been proposed to provide a dynamic change in focus, these prior approaches can be less than ideal in at least some instances. It has been proposed to provide a dynamic change in focusing power of the optic using electric voltage to provide the energy and electronic sensing to monitor physiological trigger responses, for example, electronic eye glasses and intraocular lenses comprising a dynamic add power. However, such electronic approaches can be more complex than would be ideal. Electronic control of the optical properties of the lens optic and sensing of the physiological trigger can add substantial complexity to the design and manufacturing process of such products in at least some instances.

Multifocal contact lenses have been proposed with at least two or more optical zones of different focal lengths, and such lenses are less than ideal in at least some instances. Vision correction can be provided by multifocal contact lenses that have optical zones of different focusing power disposed radially symmetrically about the optical center of the lens. However, such multifocal contact lenses can degrade vision, as the light from the portions of the lens having both focal lengths may not both be in focus. Far objects can be in focus with the part of the lens for far vision, and yet also blurred with the part of the lens for near vision. While near vision may improve with such lenses with the part of the lens for near vision, the part of the lens for far vision can also blur the image of the near object.

Although alternating vision lenses have been proposed, the vision provided with such lenses can be less than ideal in at least some instances. Alternating vision can be provided by designs in which the optical zones are separated from each other. The optical center of each zone comes in alignment with the pupillary center as the lens is translated upwards during downward gaze and translated downward during upward gaze. However, it can be difficult for a user to translate such lenses and user satisfaction and control with this sliding approach can be less than ideal.

Although accommodating contact lenses with fluidic coupling have been proposed, the results with such lenses can be less than ideal. The prior accommodating fluidic contact lenses can have less than ideal optical surfaces, as the shapes of the prior accommodating contact lenses for near vision can be less than ideal in at least some instances. Work in relation to embodiments suggest that inflation of the central portion of the prior art fluidic accommodating lenses caused by an increase in hydraulic pressure may lead to optical distortions of the anterior surface. Work in relation to embodiments also suggests that the range of optical correction of the prior accommodating fluidic contact lenses can be less than ideal in at least some instances.

In light of the above, it would be desirable to provide improved accommodating contact lenses. Ideally such lenses would be easy for the user to adjust the focus, provide crisp images with sharp focus with decreased optical artifacts, be comfortable, provide extended wear, and be readily manufactured. The embodiments disclosed herein overcome at least some of the deficiencies of the prior lenses.

SUMMARY

Embodiments of the present invention provide fluidic lenses of variable optical power having an improved range of variable optical power with decreased distortion, decreased fluidic forces and pressures, and decreased fluid movement. In many embodiments, a meniscus shaped lens module comprises one or more structures that decrease an amount of pressure or force to move surfaces of the lens and increase a separation distance of anterior and posterior surfaces of the module in order to provide an increase in optical power. Although specific reference is made to a meniscus shaped lens module for accommodating contact lenses, the embodiments as disclosed herein will find application in many fields and optical devices such as optics, optical systems, astronomy, eye glasses, cameras, machine vision systems, robotics, intraocular lenses, aberration correction and aberration correcting lenses.

In many embodiments, the accommodating contact lens comprises an inner optical reservoir comprising an anterior membrane having a pattern such as varying thickness profile. The pattern such as the varying thickness profile can correct optical aberrations when the anterior membrane moves anteriorly to a near vision configuration. The pattern of the anterior membrane can be configured in many ways and may comprise one or more of the varying thickness profile of the anterior membrane, protrusions of the anterior membrane surface, channels of the anterior membrane surface, steps of the anterior membrane, a smooth continuously curved thickness profile of the anterior membrane, steps of the anterior membrane, or undulations of the anterior membrane. In many embodiments, the near vision profile of the anterior membrane comprises an aspheric surface in order to decrease an amount of fluid received by the inner optical reservoir to provide the near vision correction. In many embodiments, the anterior membrane comprises a convex anterior surface and a concave posterior surface when the inner optical reservoir comprises a far vision profile. The pattern of the anterior membrane allows a thinner membrane that can significantly decrease an amount of pressure to increase curvature of the convex anterior surface from the convex far vision profile to a more convexly curved near vision profile.

In many embodiments, a lens structure comprises one or more a pattern of a surface of a central chamber defined with the inner optical reservoir, a meniscus, a reduced diameter or a soft material in order to provide increased amounts of curvature of an outer lens surface with decreased amounts of pressure. The increased amounts of curvature with decreased pressure can be well suited for use to deflect a curved surface from a first curvature to a second curvature, such as deflection of a curved surface of a meniscus lens from a first curvature to a second curvature, in order to provide changes in optical power and focus images over an extended range of optical power. In many embodiments, the lens structure comprises an optically transmissive covering material having an index of refraction similar to the anterior membrane such as a hydrogel disposed over pattern. The optically transmissive covering material comprises a corresponding variation in thickness extending between an anterior optical surface of the contact lens and the pattern in order to provide optical smoothness of one or more surfaces of the lens structure such as an anterior surface of the contact lens. In many embodiments, a fluid of the fluidic material of the module comprises an index of refraction similar to an index of refraction of the covering material in order to inhibit degradation of images and light scatter. The varying thickness of the covering material over the pattern can inhibit optical artifacts of the pattern that would otherwise be perceptible to the wearer.

The pattern can be formed in one or more of many ways, and may comprise one or more of folds, undulations, bellows or concertinaed surface of an optically transmissive material having a substantially uniform thickness such as a sheet of a membrane material. In many embodiments, the pattern comprise a radially extending pattern, and the distances between peaks of the pattern can vary in order to provide an optically corrective shape when the outer lens surface comprises an increased curvature in order to provide optical power. Alternatively or in combination with the pattern, the thickness of the optically transmissive material of the anterior membrane of the module under the covering material can vary to provide an optically corrective shape. In many embodiments, the shape changing optical lens structure comprises dimensions in order to increase optical correction. The materials may comprise soft material in order to increase curvature of the anterior surface when the lens deflects.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 12A shows modeling of the fluid flow through the micro-channel, in accordance with embodiments;

FIG. 22B shows example specifications of the fluidic module, in accordance with embodiments;

DETAILED DESCRIPTION

Figure 1:
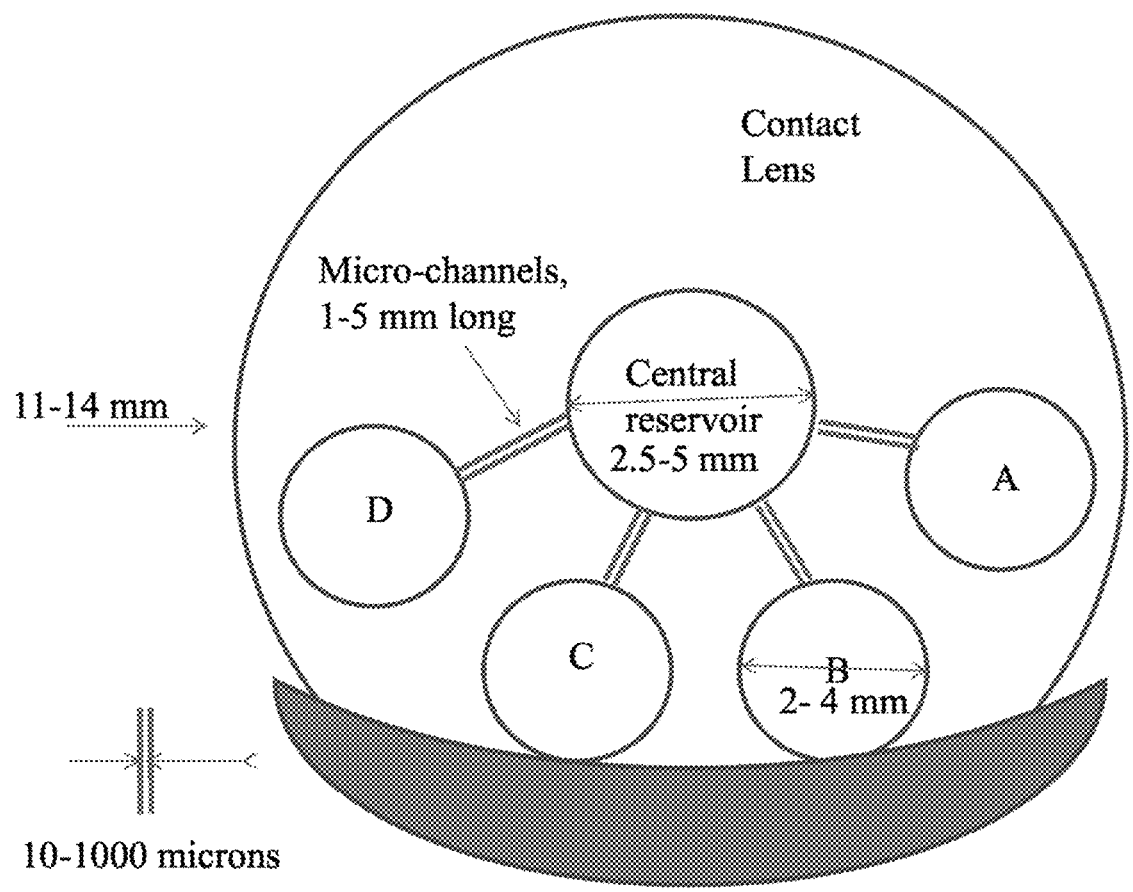
FIG. 1 shows a top view of the fluidic module, comprising a central chamber and several peripheral chambers, interconnected via micro-channels, upon primary gaze, in accordance with embodiments.

To address at least some of the problems of the prior art lenses, disclosed herein is an improved fluidic module that may be embedded into a soft contact lens for correction of presbyopia.

In many embodiments an accommodating soft contact lens comprises an embedded fluidic module capable of dynamically changing power. This module can be hermetically sealed so that substantial amounts of the fluid cannot escape the module, and can therefore be used to convey hydrostatic pressure from one part of the module to other parts of the module.

In many embodiments, the module comprises a central radially symmetric reservoir connected to a peripheral reservoir that is compressed by lower eyelid tension upon a magnitude of down-gaze that is consistent with near vision.

As used herein, the terms peripheral and outer are used interchangeably.

As used herein, the terms center and inner are used interchangeably.

As used herein top of the contact lens refers to the anterior surface, away from the corneal surface, and bottom refers to the posterior surface, closest to the corneal surface.

The outer reservoir near the periphery of the lens can be compressed upon down-gaze, leading to an increase in hydrostatic pressure of the fluid and causing fluid to be injected into the central portion of the module. Movement of the fluid into the central portion of the module causes the surface of the module to be inflated leading to an increase in curvature of the central portion of the lens aligned to the optic axis of the eye.

In many embodiments, the accommodating contact lens comprises a mechanical structure to inhibit aberrations. In many embodiments, the accommodating contact lens a mechanical structure of the anterior membrane of the central reservoir that provides to a spherical or near spherical shape upon inflation.

In many embodiments, the outer (peripheral) reservoir is located on the contact lens so that its boundaries coincide with the range of locations of the contact area of the lower eyelid with the contact lens during down-gaze.

In many embodiments, the area and the volume of the peripheral reservoir are arranged in order to provide a binary change of optical power of the contact lens that follows a binary configuration of near and far vision correction, so that a wide range of eyelid tensions and gaze angles cause similar inflation of the central reservoir in order to provide similar amounts of near vision correction. The binary configuration for near and far vision may comprise a far vision configuration for far vision and a near vision configuration for near vision. The near vision configuration may comprise a near vision profile of the anterior membrane and the far vision configuration may comprise a far vision profile of the anterior membrane. In many embodiments, additional pressure to the outer (peripheral) chamber may provide no substantial increase in optical power. While this inhibited increase in optical power can be provided in many ways, in many embodiments, the volume of the outer (peripheral) reservoir is sized such that the volume of the outer reservoir corresponds to the maximum optical correction of the near vision configuration, which can make the accommodating contact lens easier to use. In these binary embodiments, additional pressure may provide no substantial increase in optical power when the module comprises the near vision configuration.

The inventors have conducted laboratory, clinical and numerical modeling studies in order to determine structures of an accommodating contact lens that overcomes deficiencies of the prior accommodating contact lenses.

Design of the Fluidic Module

FIG. 1 shows a top view of the fluidic module, comprising a central chamber and several peripheral chambers, interconnected via micro-channels, upon primary gaze.

Figure 2:
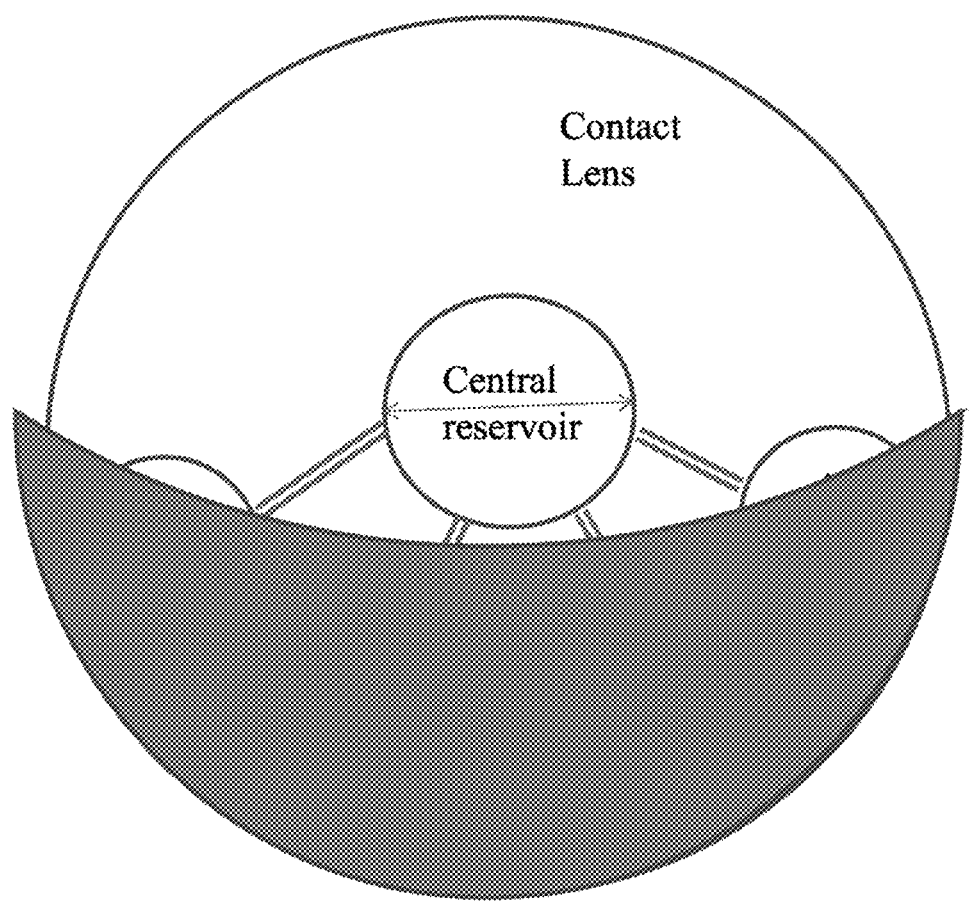
FIG. 2 shows a top view of the fluidic module, comprising a central chamber and several peripheral chambers, interconnected via micro-channels, upon downward gaze, in accordance with embodiments.

FIG. 2 shows a top view of the fluidic module, comprising a central chamber and several peripheral chambers, interconnected via micro-channels, upon downward gaze.

Figure 3:
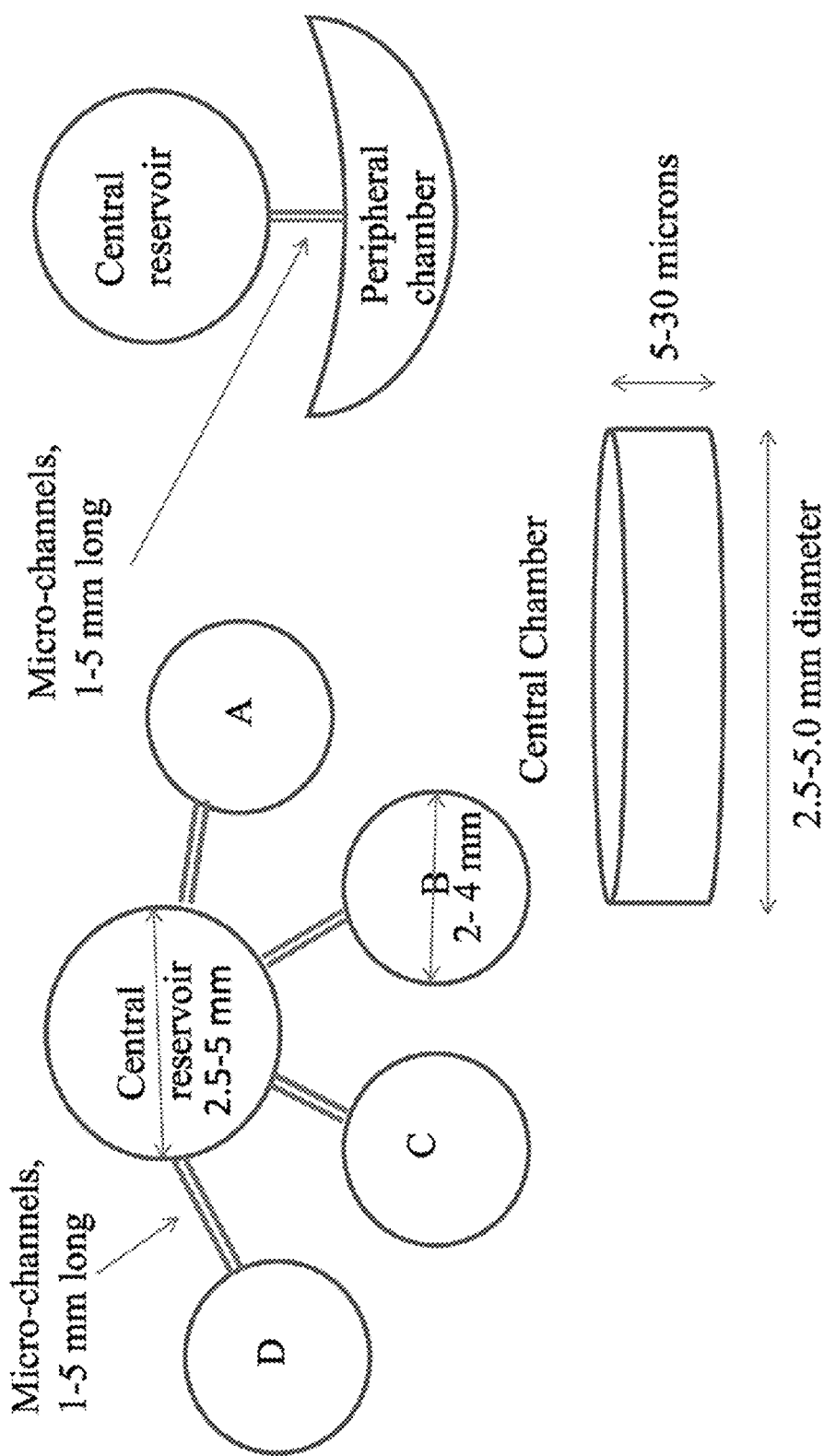
FIG. 3 shows examples of designs of the fluidic module and chambers, in accordance with embodiments.

FIG. 3 shows examples of the fluidic module and chambers.

The fluidic module can be embedded in the soft contact lens such that the module is close to the anterior (convex) surface of the lens.

In many embodiments, there is a thin layer of contact lens material above the fluidic module, its thickness being in the range of 5-50 microns, for example.

Being close to the surface of the contact lens, a change in curvature of the fluidic module (caused by inflation or deflation through fluid transfer between the central and peripheral chambers) causes a corresponding change in the anterior curvature of the soft contact lens.

In many embodiments, the diameter of the central chamber is within a range from about 1.0 to 5.0 mm, for example, while the depth of the fluid is within a range from about 10-40 microns. The diameter of the central chamber and corresponding optically transmissive accommodative structure can be within one or more of many ranges for example from about 1.5 to 2.5 mm or within a range from about 2.5 to 5 mm, for example. Work in relation to embodiments suggests that decreased diameter can provide increased optical power for comparable amounts of fluidic movement and pressure, for example, which can be beneficial with curve meniscus embodiments as described herein, for example.

The thickness of the membranes comprising the top and the bottom surfaces of the central chamber can be in within a range from about 5 to 50 microns, for example.

The central (inner) reservoir chamber may comprise a diameter within a range from about 2.5 to 5 um. The central reservoir chamber may comprise a thickness within a range from about to 30 um. The side walls of the chamber can be annular, for example, in order to define a rotationally symmetric optical surface. In many embodiments, the side walls of the chamber add stiffness to define the optical surface of the anterior membrane in the near vision configuration. In many embodiments, the annular walls of the central chamber fix the outer boundary of the anterior membrane in order to provide a fixed reference frame and deflect the anterior membrane with a predetermined surface profile. In many embodiments, the annular walls of the chamber comprise a stiffness greater than the anterior membrane in order to inhibit distortions of the annular membrane.

The anterior membrane may comprise a thickness within a range from about 2 um to about 10 um, and the posterior membrane may comprise a thickness within a range from about 5 um to about 30 um, for example. In many embodiments, the posterior membrane comprises a thickness greater than the anterior membrane, and the soft contact lens material over the posterior membrane along a posterior surface of the contact lens comprises a thickness greater than the soft contact lens material along an anterior surface of the contact lens over the anterior membrane.

In many embodiments, the annular sidewall of the inner reservoir chamber is affixed to each of the upper membrane and the lower membrane.

In many embodiments, the outer (peripheral) reservoir chamber comprises anterior and posterior membranes having thicknesses and structures similar to the inner (central) reservoir chamber.

Design and Simulation of the Central Module

The fluidic module is provided to conform to the curvature of a soft contact lens when encapsulated into one.

Since the radius of curvature of a typical soft contact lens is about 7.5 mm to 9.5 mm, the shape of the fluidic module will be meniscus like in many embodiments.

Figure 4:
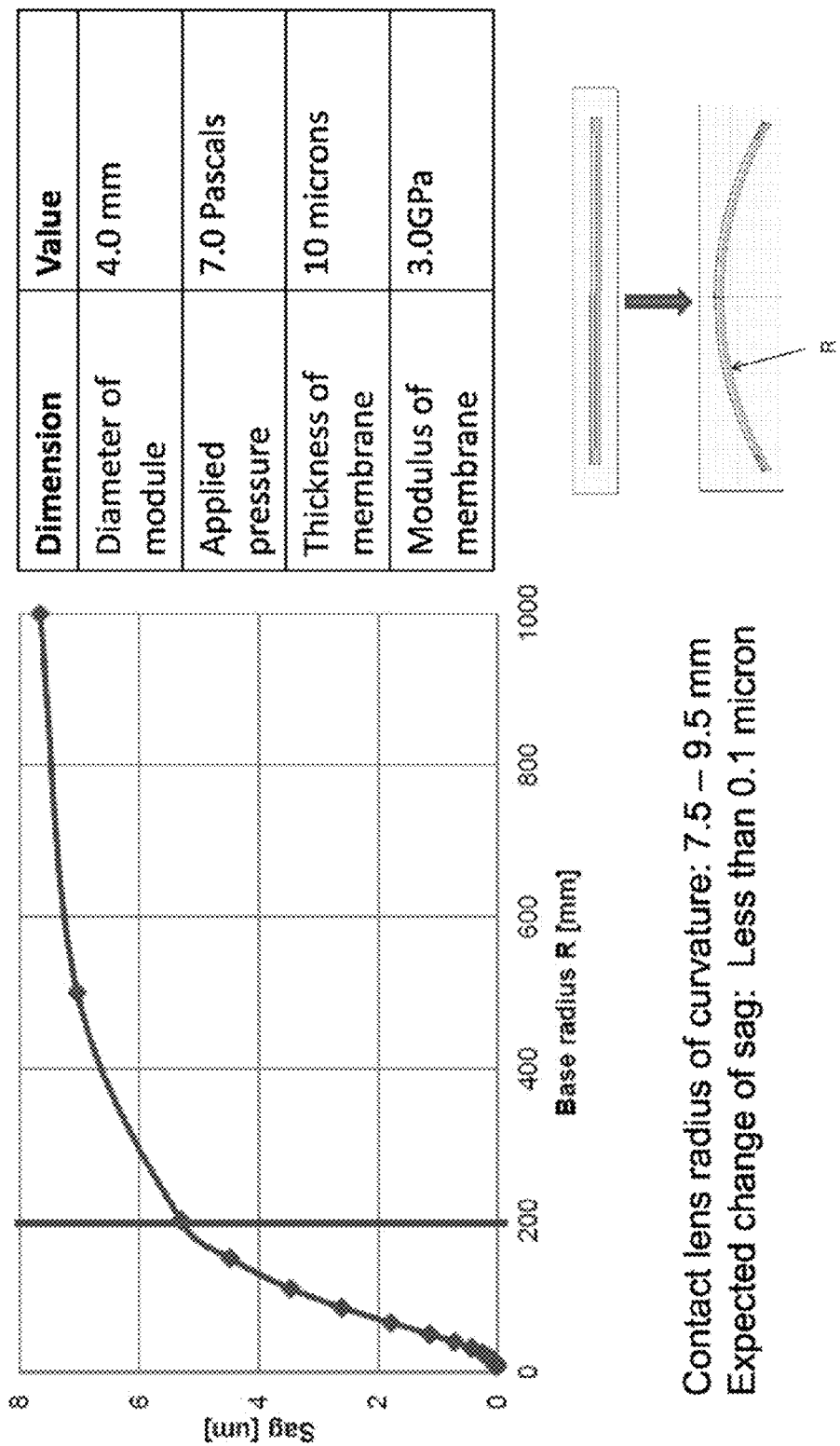
FIG. 4 shows dependence of sag changes in a round fluidic module due to an increase in hydrostatic pressure modeled as a function of radius of curvature of the module, in accordance with embodiments.
Figure 5:
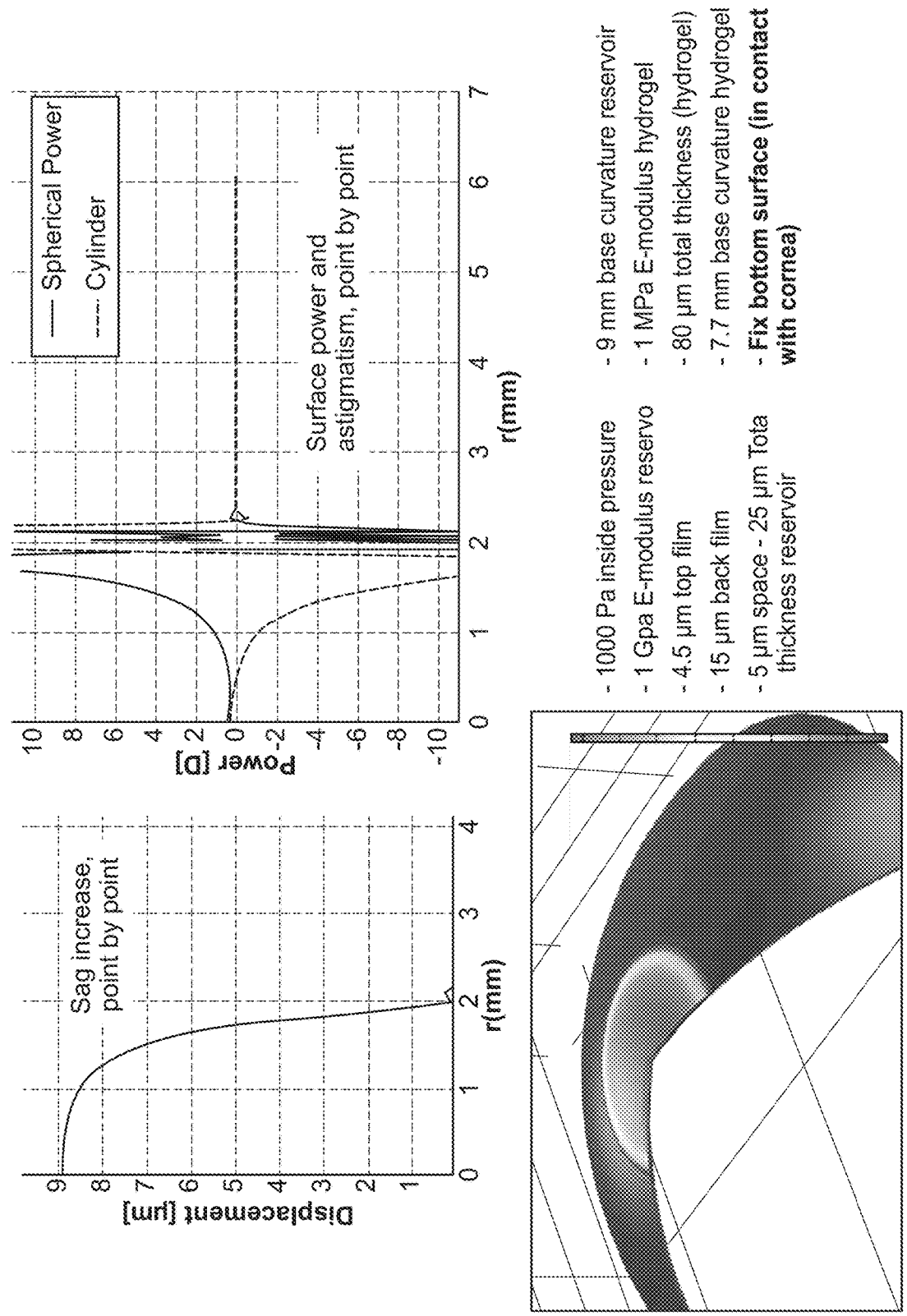
FIG. 5 shows shape of the inflated membrane and corresponding change in optical power of the module across the module surface, in accordance with embodiments.

It is therefore helpful to model the inflation of a meniscus shaped round fluidic module upon injection of additional fluid into it from peripheral reservoirs, by means of microchannels, as shown in FIGS. 4 and 5.

FIG. 4 shows that inflation or increase in sag caused by a specific amount of hydrostatic pressure is strongly dependent on the radius of curvature of the module.

In accordance with the embodiments of FIG. 4, it is clear that change in sag of the anterior membrane of a module will require a much greater pressure when the module is meniscus shaped, relative to a flat configuration.

Moreover, the change in sag is highly aspheric, causing an optical power profile that is not constant across the whole surface, as shown in FIG. 5.

FIG. 4 shows dependence of sag changes in a round fluidic module due to an increase in hydrostatic pressure modeled as a function of radius of curvature of the module.

FIG. 5 shows shape of the inflated membrane and corresponding change in optical power of the module across the module surface.

Figure 6:
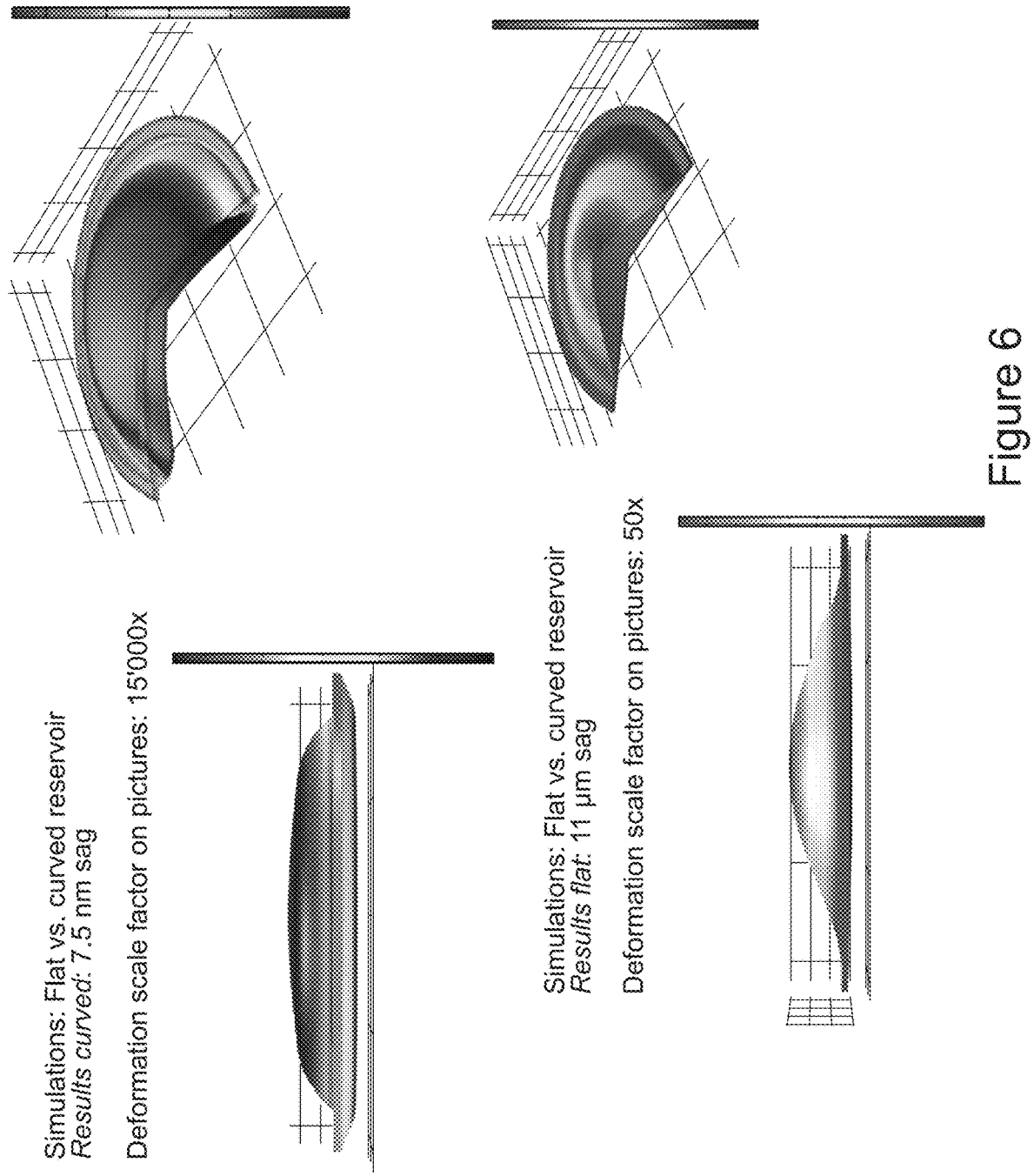
FIG. 6 shows simulation of deformation modes of the anterior membrane of the central module as a function of radius of curvature of module (Tensile modulus of membrane is 1.9 GPa in this simulation), in accordance with embodiments.

FIG. 6 shows simulation of deformation modes of the anterior membrane of the central module as a function of radius of curvature of module (Tensile modulus of membrane is 1.9 GPa in this simulation).

Figure 7:
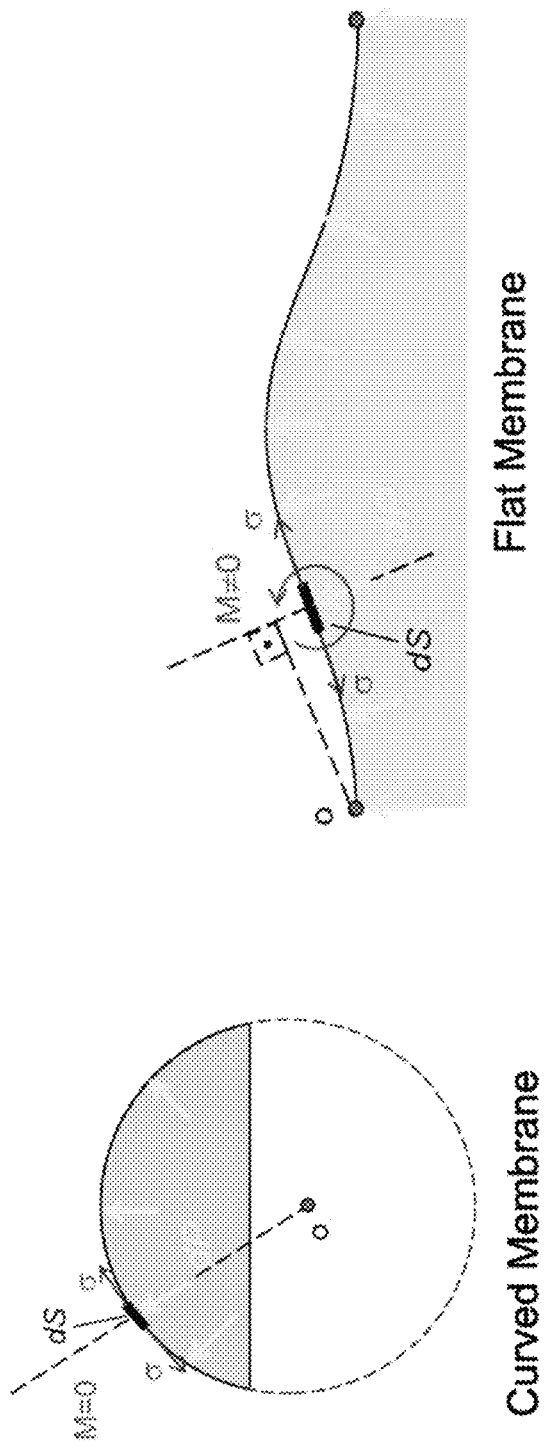
FIG. 7 shows different modes of deformation are activated when the membrane of the central module is flat or curved, in accordance with embodiments.

FIG. 7 shows different modes of deformation that are activated when the membrane of the central module is flat or curved.

Figure 8:
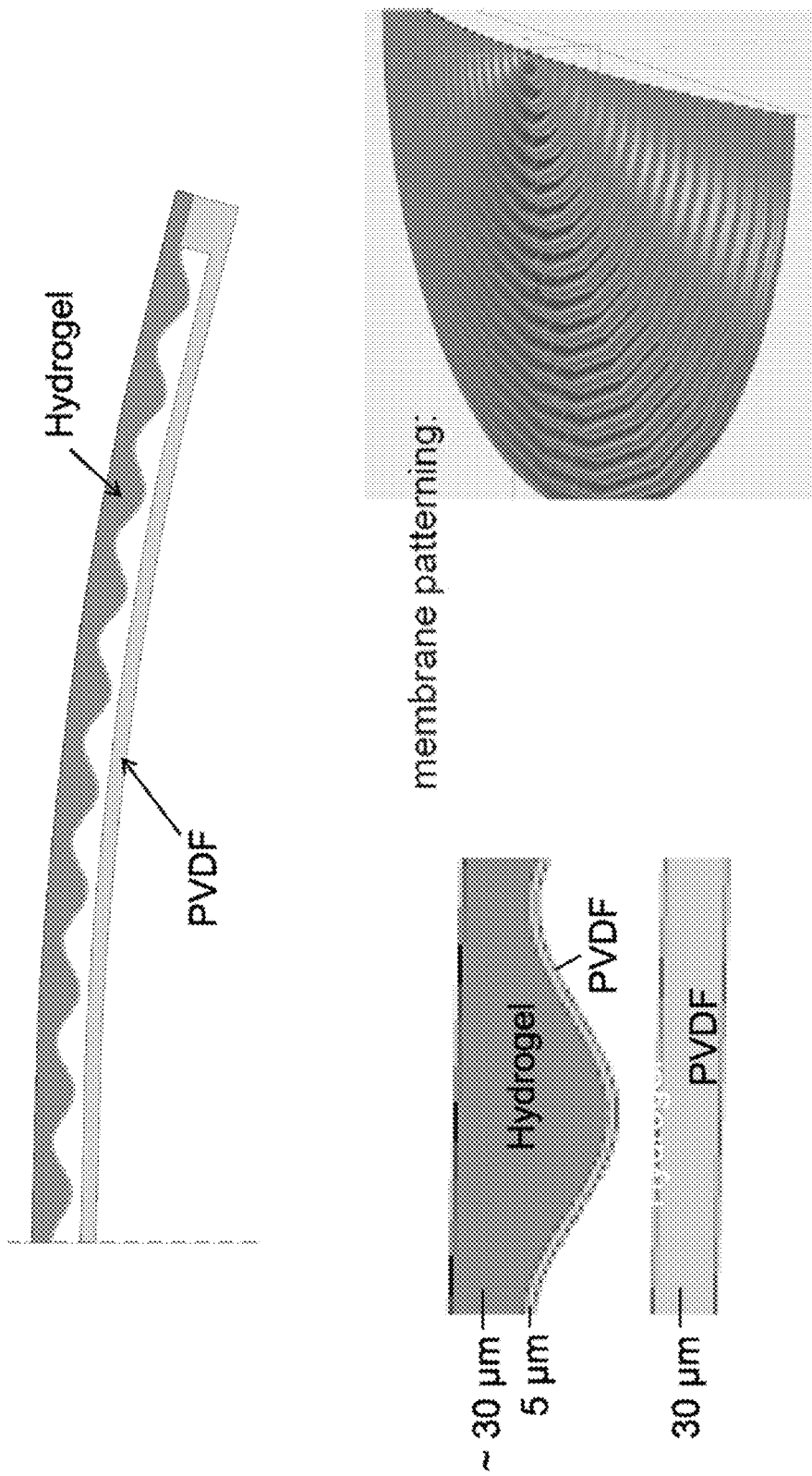
FIG. 8 shows patterning of the membrane in accordance with embodiments.

FIG. 8 shows patterning of the membrane. The patterning process and corresponding structure can be formed in one or more of many ways such as one or more of thermoforming of a spun or stretched membrane, for example. The soft contact lens material comprising a hydrogel comprises a varying thickness profile extending between an anterior surface of the contact lens and an anterior surface of the anterior membrane in order to inhibit optical artifacts such as light scattering of the pattern such as the undulating pattern shown.

Figure 9:
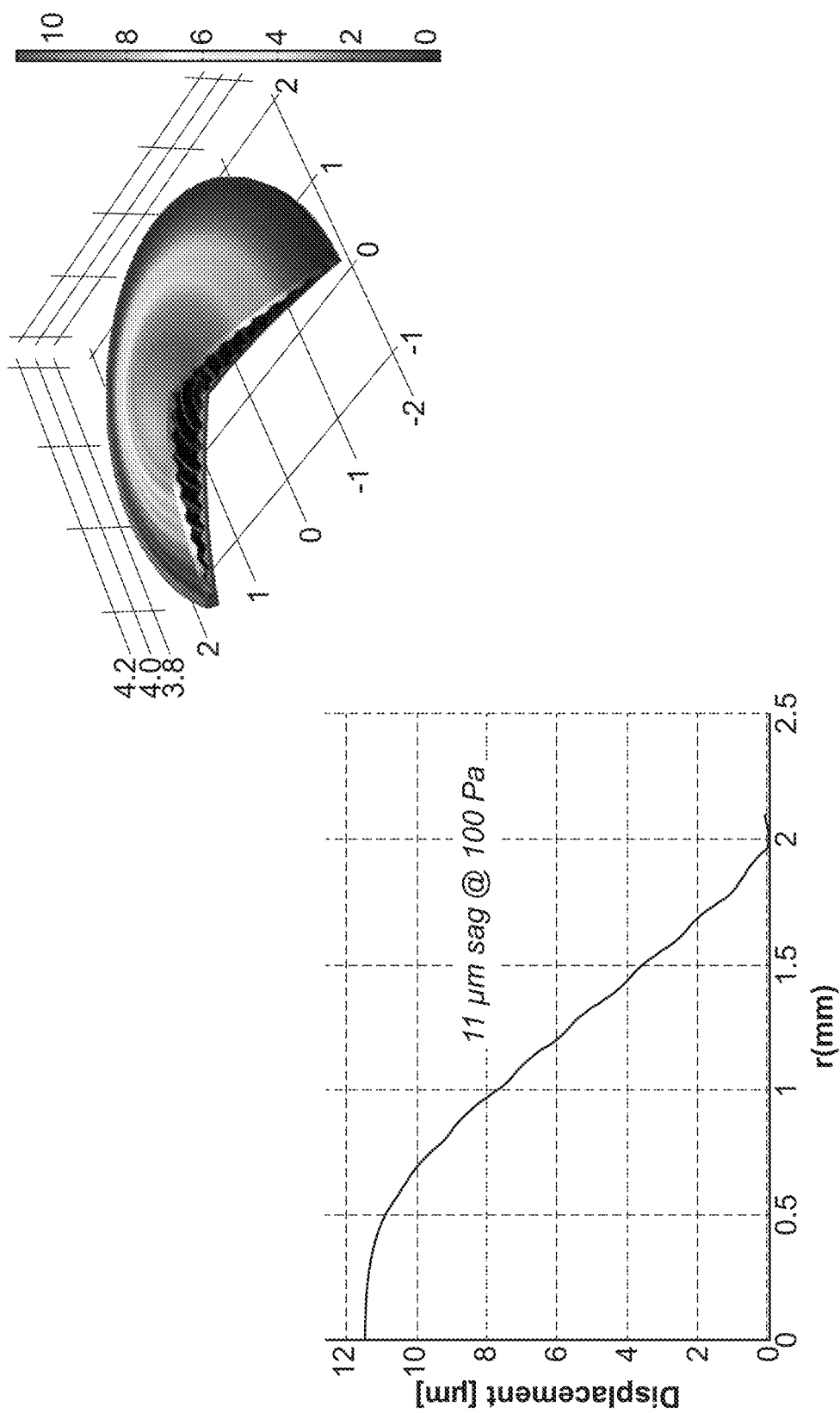
FIG. 9 shows simulation of the mechanical response of a patterned membrane of the central module, in accordance with embodiments.

FIG. 9 shows simulation of the mechanical response of a patterned membrane of the central module.

Figure 10:
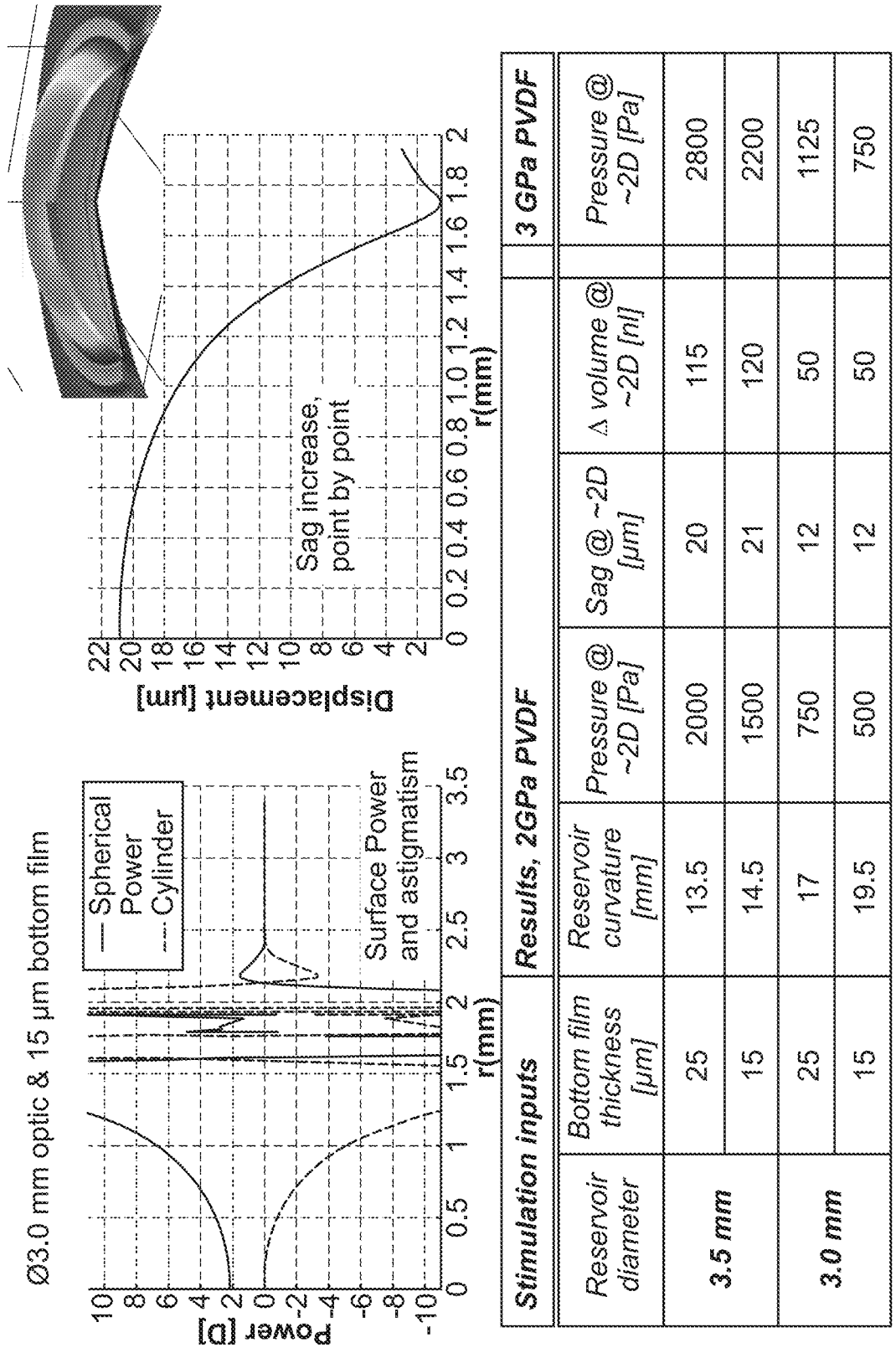
FIG. 10 shows effects of reducing the diameter of the central module, in accordance with embodiments.

The analysis, shown in Figures as described herein such as FIGS. 9 and 10 demonstrate that the central module can develop an unacceptable level of spherical aberration, unless the mechanical response of the surface to hydrostatic pressure is somehow altered in order to ensure a more uniform change in optical power across the surface.

This difference in mechanical response of the membrane as a function of its radius of curvature is shown in FIG. 6.

The main reason is shown in Figures described herein such as FIG. 7. These show that while a flat membrane undergoes deformation in response to a hydrostatic pressure mainly in the form of a flexure, a meniscus shaped membrane undergoes deformation mainly in the form of extension (stretching).

This problem may be solved in a number of ways with one or more of many structures as described herein, and these structures can be combined in accordance with embodiments.

The first preferred approach is to use a patterned membrane, as shown in FIG. 8, for example, in accordance with embodiments.

The pattern allows the membrane to respond to hydrostatic pressure by undergoing flexure rather than stretching.

It increases substantially the total sag change as a function of hydrostatic pressure, and also provides a method to modulate the change of optical power across the surface of the membrane. The pre-patterning approach is preferred because it allows the use of central modules that are 3.5 mm and greater in diameter.

The impact on the retinal image is expected to be negligible, since the optical effect of the patterned surface is nullified by the presence of the hydrogel layer that matches the membrane in refractive index.

A second preferred method to solve the design problem is to use a module with a smaller diameter, in accordance with embodiments.

For example, reduction of the diameter of the central module from 3.5 mm to 3.0 mm substantially reduces the force provided to deform the membrane in order to achieve the required change in sag.

It also reduces the asphericity of the deformed membrane, as shown in FIG. 10.

In addition, it requires less fluid to cause a change in sag, so that a greater dynamic range in optical power becomes available.

FIG. 10 shows the effect of reducing the diameter of the central module.

A third preferred method to vary the thickness of the membrane across the surface of the module, in accordance with embodiments.

For example, it is possible to use an anterior membrane that is 15-50 microns in thickness at the periphery, and 5 microns in thickness at the center.

Such a membrane of variable thickness may be formed by extrusion or thermoforming, for example.

Figure 11:
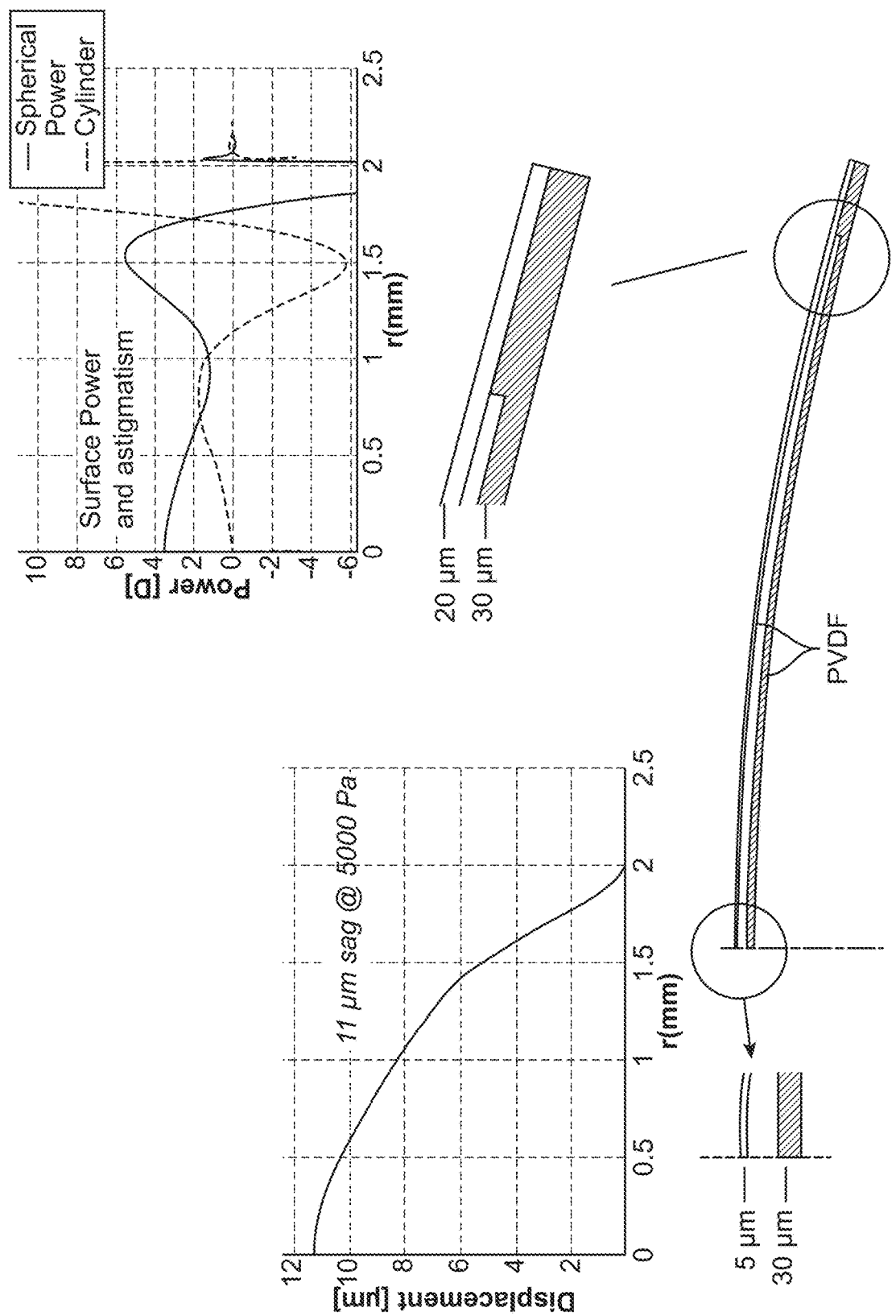
FIG. 11 shows the effect on the deformation mode and optical power increase of a central module comprising a membrane of variable thickness, in accordance with embodiments.

FIG. 11 shows the effect on the deformation mode and optical power increase of a central module comprising a membrane of variable thickness.

The simulation shows that this would be an effective approach for a membrane material with a lower tensile (or E) modulus.

FIG. 11 shows the effect of membrane thickness variation on the deformation characteristics and sag change upon application of hydrostatic pressure.

A fourth preferred method is to reduce the tensile modulus of the membrane comprising the liquid lens module, in accordance with embodiments.

Analysis indicates that reduction of the modulus of the membrane from 3 GPa to 2 GPa substantially reduces the pressure required to cause an equivalent change in sag.

At least some embodiments may use a softer, elastomeric material such as PDMS (polydimethyl siloxane) that has a E modulus in the range 1.0 to 300 MPa.

Other embodiments may use a copolymer of PVDF that decreases the E modulus by a factor of 2-5.

In many embodiments, a decrease in modulus, causing a decrease in the barrier properties of the membrane, in other words, membranes made from either type of material will have higher diffusion coefficients for the silicone oil and other fluids used herein.

These membranes may be coated with a thin layer of a material that can function as a diffusion barrier, such as Paralyne™. In some embodiments 2 two layers of different material are used for the anterior membrane and the central chamber, for example.

Therefore, use of Paralyne™ coated PDMS or other more flexible fluorocarbon materials will provide the required change in sag needed for a 3.0 diopter increase in optical power.

Change of sag and hence optical power in the central module is effected by a flow of fluid from peripheral modules and the attendant increase in hydrostatic pressure, in accordance with embodiments.

The two parameters that can be controlled in order to achieve specified change of sag in the central module are the pressure exerted by the lower eyelid, and the amount of fluid that is squeezed out of the peripheral modules.

The resistance to flow presented by the one or more channels such as the micro-channel controls the period of response, and also the amount of fluid that ultimately enters the central module as a result of eyelid pressure.

A hydrodynamic model was created to estimate the period of response.

It was found that the cross section of the channel, especially its two dimensional cross section, and the viscosity of the fluid were the two most important controlling parameters, while the length of the micro-channel was much less important, in accordance with embodiments.

Reduction of viscosity certainly can reduce response time, but may require a greater increase in sag change in order to achieve an increase in optical power.

It is therefore helpful to determine a suitable trade-off between the response time and the fluid volume required to provide change in optical power.

Figure 12:
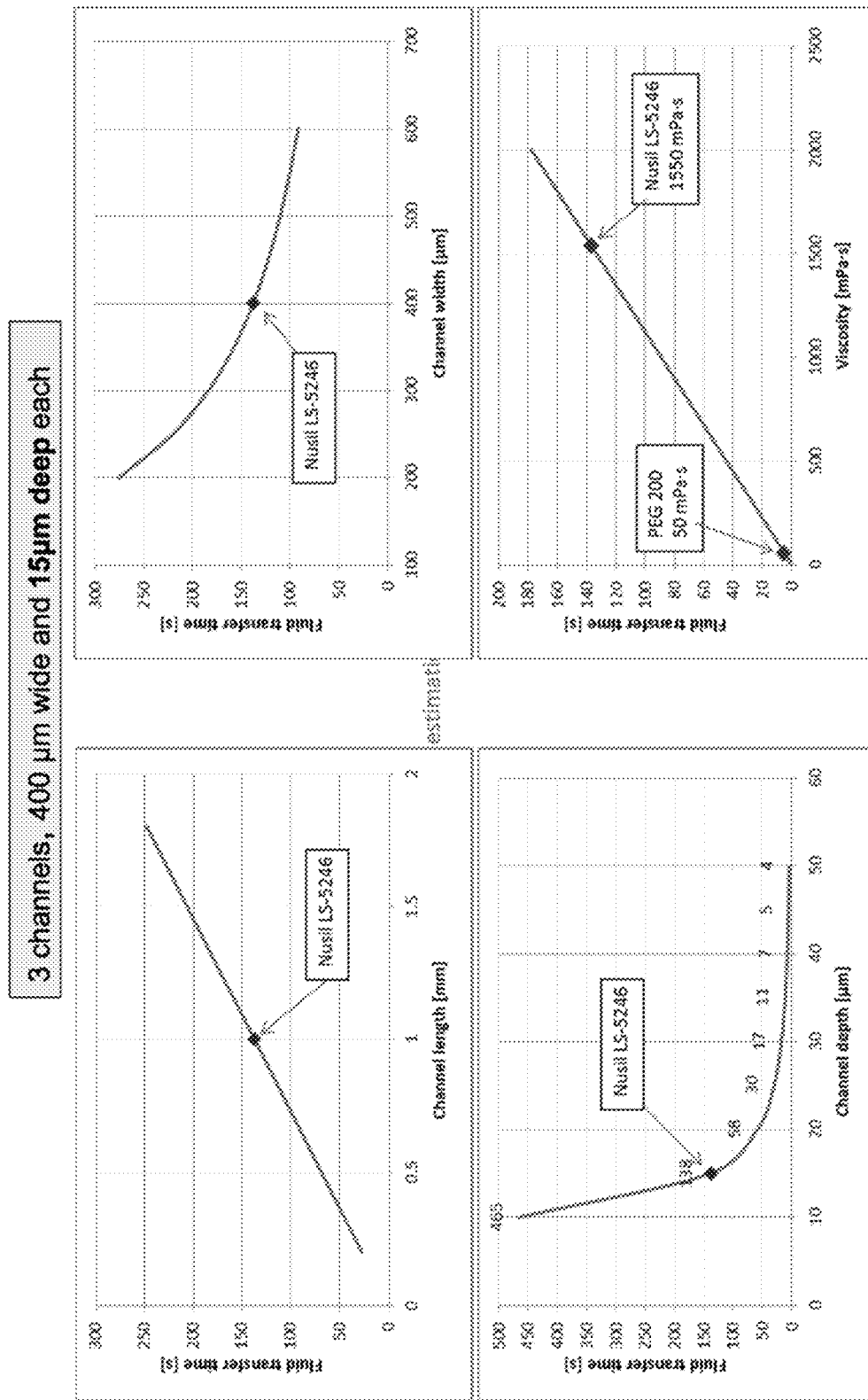
FIGS. 12 and 13 show the results of simulation of fluid flow as a function of viscosity of fluid and dimensions of the micro-channel, in accordance with embodiments.
Figure 12:
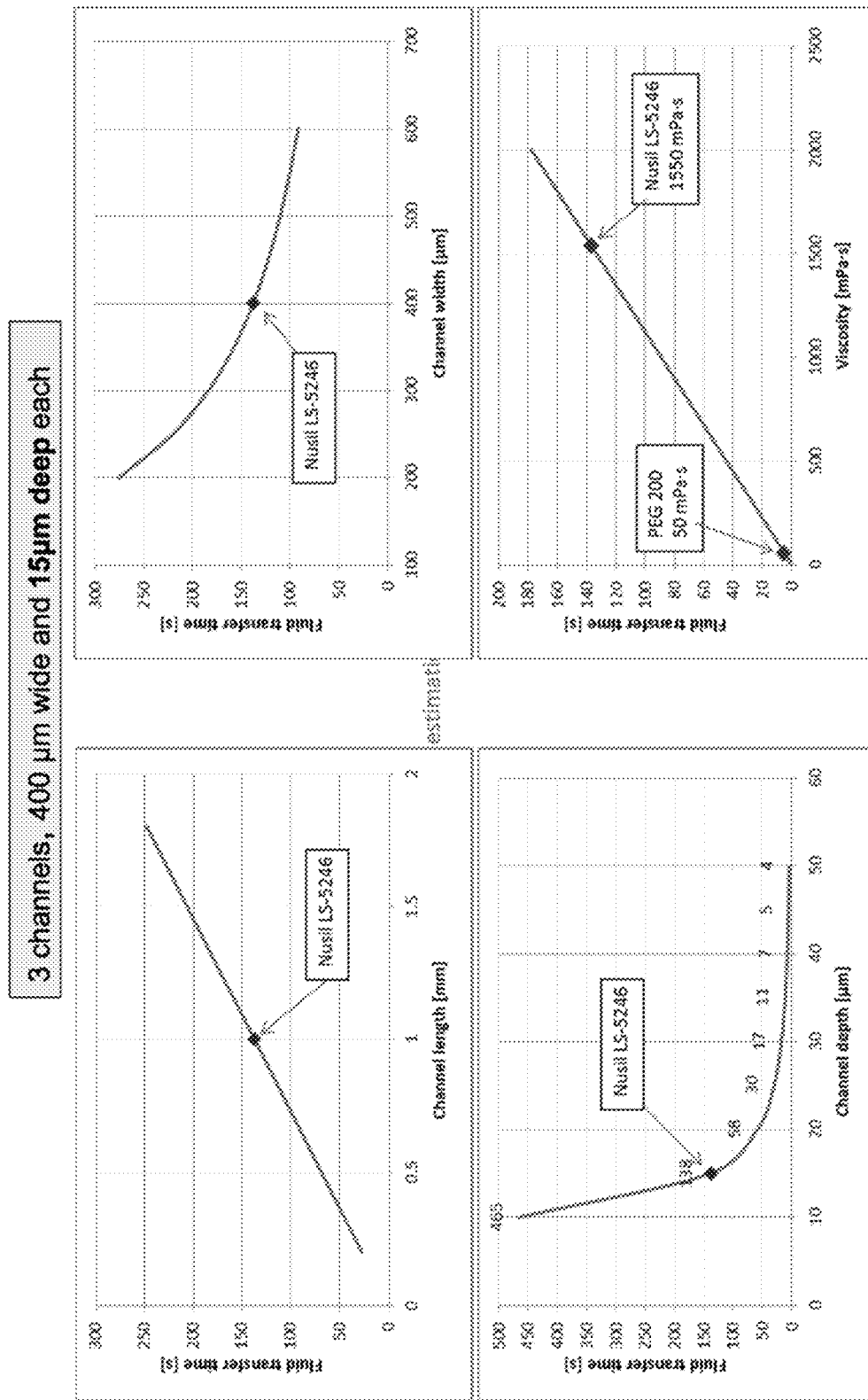

This optimization is achieved by developing a model based on Navier's Stokes equation, as shown in FIGS. 12 and 12A.

Figure 13:
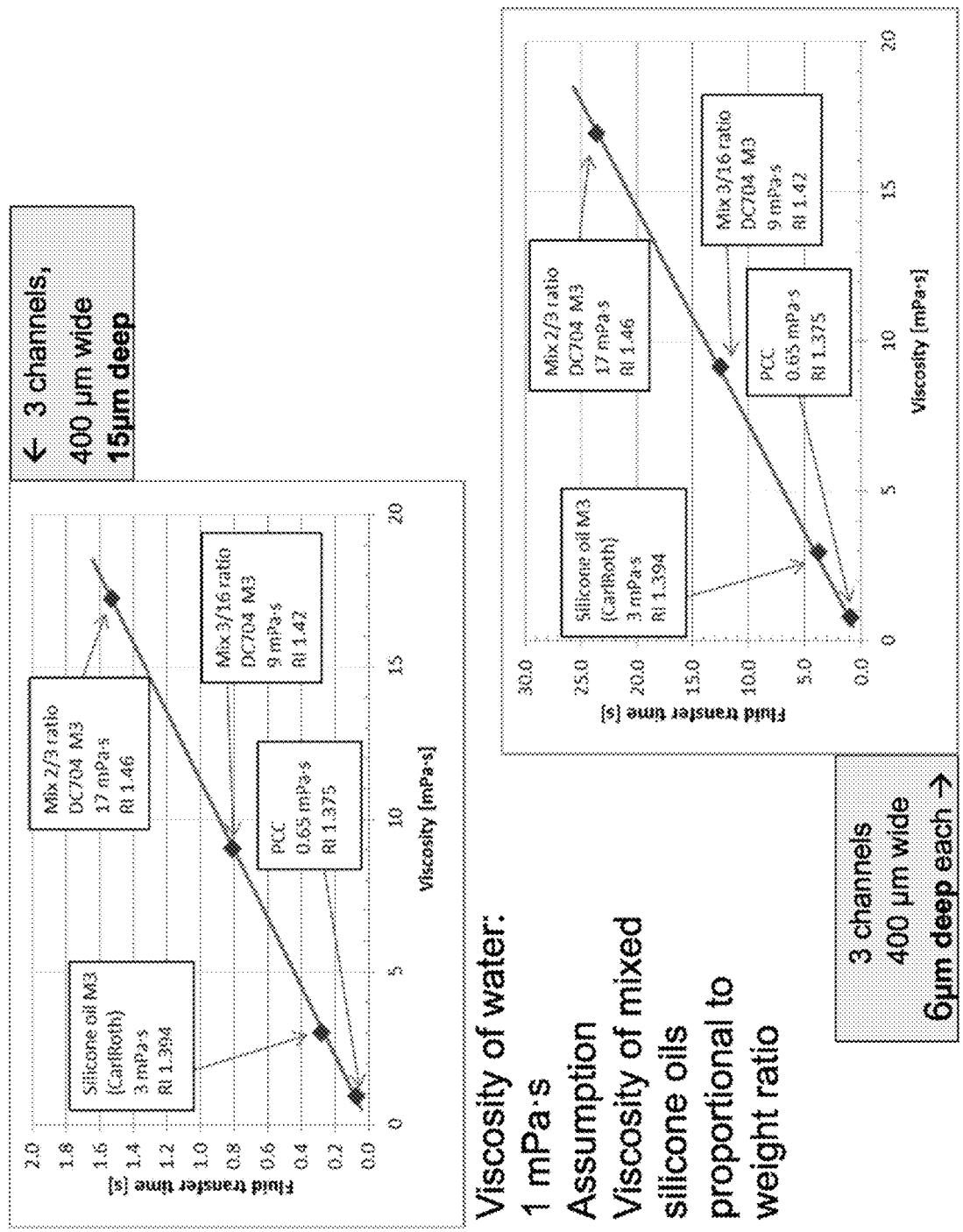

FIGS. 12 and 13 also show the results of simulation of fluid flow as a function of viscosity of fluid and dimensions of the micro-channel.

The model indicates that a trade off or optimization is required between refractive index and viscosity of the fluid and the dimensions of the micro-channel.

This is because there is a positive correlation between viscosity and refractive index of silicone oils preferred for application as a fluid, while the two key parameters that affect response time are viscosity and fluid depth in the absence of applied pressure.

A response time of 1.5 seconds or less calls for an upper limit of 5.0 cst in the dynamic viscosity of the fluid, measured at 25 C.

A fluid with a viscosity of less than 1 cst is likely to have a higher diffusion coefficient as well as a lower refractive index.

The preferred range of viscosity of the fluid is therefore 1-5 cst.

The most preferred refractive index of the fluid is equal to the refractive index of the contact lens in which the module is encapsulated.

Lowering the refractive index of the fluid below 1.37 can have less than ideal results, since the refractive index of hydrated soft contact lenses can be 1.41 or higher, all measured at 530 nm.

Among the less than ideal results are the module providing additional fluid to reach the same targeted increase in optical power of the contact lens during down-gaze.

Also, there is a positive correlation between refractive index and specific gravity of the fluid.

This correlation may drive the specific gravity of silicone oils below 0.9 g/cc as refractive index drops below 1.39.

In many embodiments, during encapsulation of the module in the soft contact lens, it is desirable to achieve a close match between the specific gravity of the hydrated soft contact lens and the module, typically at about 1.0 g/cc.

The preferred range of specific gravity of the fluid comprising the module is 0.95 to 1.05 g/cc.

Based on this trade-off, a silicone oil with a viscosity of 2.0-3.0 cst at 25 C and refractive index of 1.39 was helpful for this application, while a range of viscosity from 1.0-5.0 cst is also helpful, with a fluid depth in the range of 7-20 microns.

Estimation of fluidic volume available and its flow rate at a particular pressure.

FIG. 12A shows modeling of the fluid flow through the micro-channel.

FIG. 12 shows dependence of flow rate (time of response) to channel depth, channel length, channel width and viscosity.

FIG. 12 also shows dependence of flow rate (time of response) to channel dimensions: close up on depth.

FIG. 13 shows dependence of response time on viscosity of fluid.

The available range of optical power in the liquid lens module depends on the volume of fluid that can be displaced, for example squeezed, out of the peripheral reservoirs.

This volume is dependent on applied pressure, the flexibility of the membrane and the total volume of the peripheral reservoirs as well as the surface area that will be subjected to compression.

The analysis indicates that use of a somewhat stiff and impermeable membrane is acceptable if the diameter of the central module is kept to a maximum of 3.0 mm, assuming a normal range of eyelid pressure (1000-2500 Pascals).

The volume provided to increase optical power by at least 2.0D is about 50 nl, while the volume required to increase power by 3.0D is approximately 80 nl.

Figure 14:
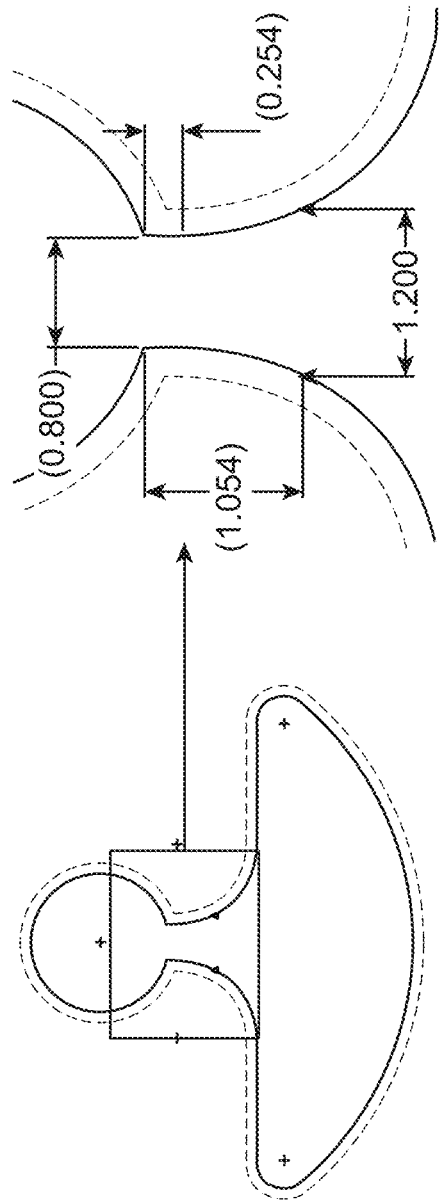
FIG. 14 shows the trade off between the pressure required to squeeze out a specific amount of fluid from a peripheral module and the stiffness of the membrane, in accordance with embodiments.

FIG. 14 shows the trade off between the pressure provided to displace, for example squeeze out, a specific amount of fluid from a peripheral module and the stiffness of the membrane.

Noting that the pressure applied by the lower lid can varies between 1000 to 2500 Pascals depending upon gaze angle and the strength of the eyelid muscles, FIG. 14 shows that the PVDF is an appropriate membrane material, in accordance with embodiments.

Modified Design of the Liquid Lens Module in Accordance with Additional Embodiments FIG. 14 shows dependence of available fluid volume on applied pressure and membrane stiffness for a particular design.

The foregoing model of fluid flow and availability of fluid volume provides guidance to two or more different design parameters.

For example, when designing a binary accommodating contact lens that achieves two well defined optical powers of correction for all individuals with a wide range of lid force, it is preferable to limit the volume of fluid that is available and match it with a received volume of fluid and corresponding the diameter of the central module, in accordance with embodiments.

A central module of diameter 3.0 mm can receive about 50 nl of fluid to achieve 2.0D of inflation.

If the peripheral reservoir is designed in such a way as to limit the outflow of fluid to 50 nl under the whole range of pressure exerted by the lower lid, (e.g., 500-2500 Pascals, e.g. 1,000 to 2,500 Pascals) then a binary (bifocal) contact lens configuration is provided in accordance with embodiments.

If the design objective is to provide a much wider range of optical powers (e.g., up to 10 diopters), use of a more flexible material can be used for the membrane comprising the liquid lens module, a material with a tensile modulus in the range 0.01 to 1.0 GPa and a larger size peripheral chamber, in accordance with embodiments.

If the design objective is to provide a specific intermediate power (for example, in the range of 1.0 to 2.0D) at smaller downward gaze angles, while providing a specific near power (for example, in the range of 2.5 to 3.5D) in a trifocal like function, then it is helpful to provide multiple peripheral reservoirs, each connected to the central module by a separate micro-channel, each of different length. In some embodiments, a plurality of channels is coupled to the central optic chamber and a plurality of separate peripheral containers, so that a first container of the plurality is engaged as the lid rises or the eye moves downward and a second container of the plurality is engaged with additional lid rise or downward movement in order to provide intermediate power.

Such a design will deliver the specified optical powers only for a narrower ranges of lower lid pressures, e.g., (1000-1500 Pascals, and 1500-2000 Pascals, etc.) achievable at a specific gaze angle, in accordance with embodiments.

This design approach can benefit from multiple design configurations or skus to serve the whole population of persons requiring vision correction throughout the world.

In many embodiments, the central chamber is cylinder shaped with edges that are relatively stiff with increased thickness, for example, its faces being covered by a relatively flexible distensible membrane. The top and bottom faces are circular in shape.

The central chamber is connected to each of the peripheral chambers by means of a one or more micro-channels, or multiple channels having a similar shape or various shapes depending on the desired flow characteristics.

The fluidic module can be located inside the soft contact lens in one or more of many ways. For example, the geometrical center of the central module lens optic can be co-linear with the geometrical center of the contact lens and the optical zone of the contact lens. Alternatively the optic of the module can be decentered with respect to the geometrical center of the contact lens body in order to align the optical axis of the module with a pupillary center of the eye, for example.

The fluidic module is filled with a biocompatible fluid, preferably of the same or similar refractive index as the material of the soft contact lens, within in the range of about 1.41 to about 1.55, for example.

The viscosity of the fluid is in the range 0.2-100 centistokes at 37 C.

The fluid is preferably a siloxane, a fluorocarbon, an ester, an ether or a hydrocarbon.

The membrane is biocompatible, and has an index preferably the same as the fluid and the contact lens itself, in the range 1.41-1.55.

The membrane may be of the same thickness throughout, or it may have a thickness profile, contoured to control its rigidity or flexibility along the dimensions of the membrane.

Each of the embodiments as described herein can be combined with one or more components of other embodiments as described herein.

In some embodiments, the module can be overfilled with fluid, which may result in a more spherical shape and increased sag under similar forces.

In some embodiments, the thickness of the thin layer of contact lens material above the fluidic module may be uniform. In some embodiments, said thickness may not be uniform. For example, the module can be placed in the contact lens so that the thin layer of material is thicker, and hence higher, at the center of the contact lens than at the edge of the central chamber. The module can then act as a piston and increase the sag of the central chamber than that the edges, increasing the sag by a greater amount than with the module alone (without the additional thickness of the thin layer of material). A thicker layer of the thin material may also provide reduced small aberrations caused by the module.

In some embodiments, the surface of the module may be bound to the contact lens material. In some embodiments, the surface of the module may be unbound to the contact lens material. In many embodiments, the surface of the module may be bound to the contact lens material in some portions, and unbound in other portions. For example, one surface of the module, such as the central chamber anterior surface, may be unbound, while the rest of the module surfaces are bound to the contact lens material.

In some embodiments, the peripheral reservoirs may comprise variable depths. For example, a peripheral reservoir may be configured to have a shallower depth, and hence hold less fluid, closer to the lower lid. Such a variable depth configuration can create a smaller sag for intermediate vision.

In some embodiments, the membrane of the central module may comprise a circular pattern. The pattern can provide a method to modulate the amount of sag in the contact lens, as different patterns can provide different amounts of sag under a similar force.

In some embodiments, the patterned membranes may also be applied to lower or peripheral chambers/modules, in order to enhance the sensitivity of the module surface. Such patterning can enable a binary optic within a broader range of lower eyelid forces. The patterning can also allow less force from the eyelid to restrict the flow of fluid back in the lower chambers, when the eyelid is in full contact with the lower chambers.

In some embodiments, the height of the pattern may be varied. For example, the height of the pattern can be increased by adding a "step", or a discrete amount of height, to another pattern, resulting in an increased height of the pattern. Such an increased height of a pattern can provide a hinge effect, which can augment the resulting sag change.

Figure 18A:
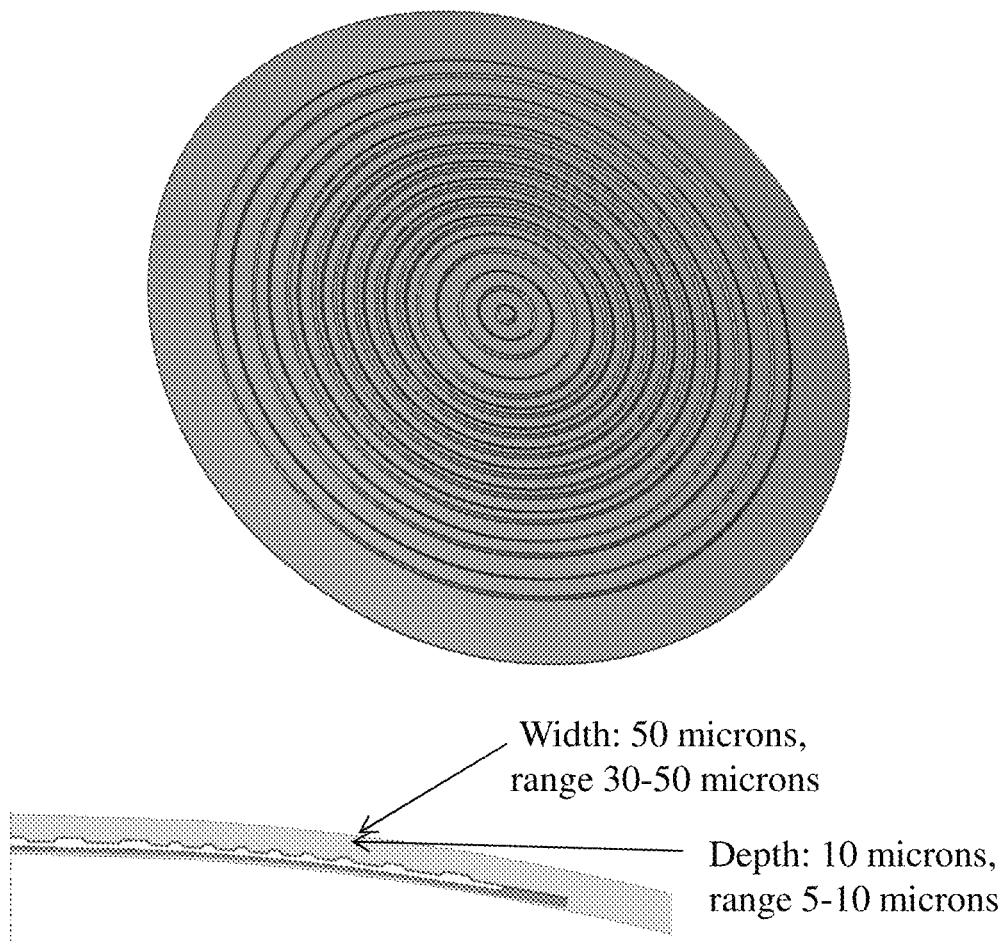
FIG. 18A shows a pattern of an accommodating contact lens membrane, in accordance with embodiments.
Figure 18B:
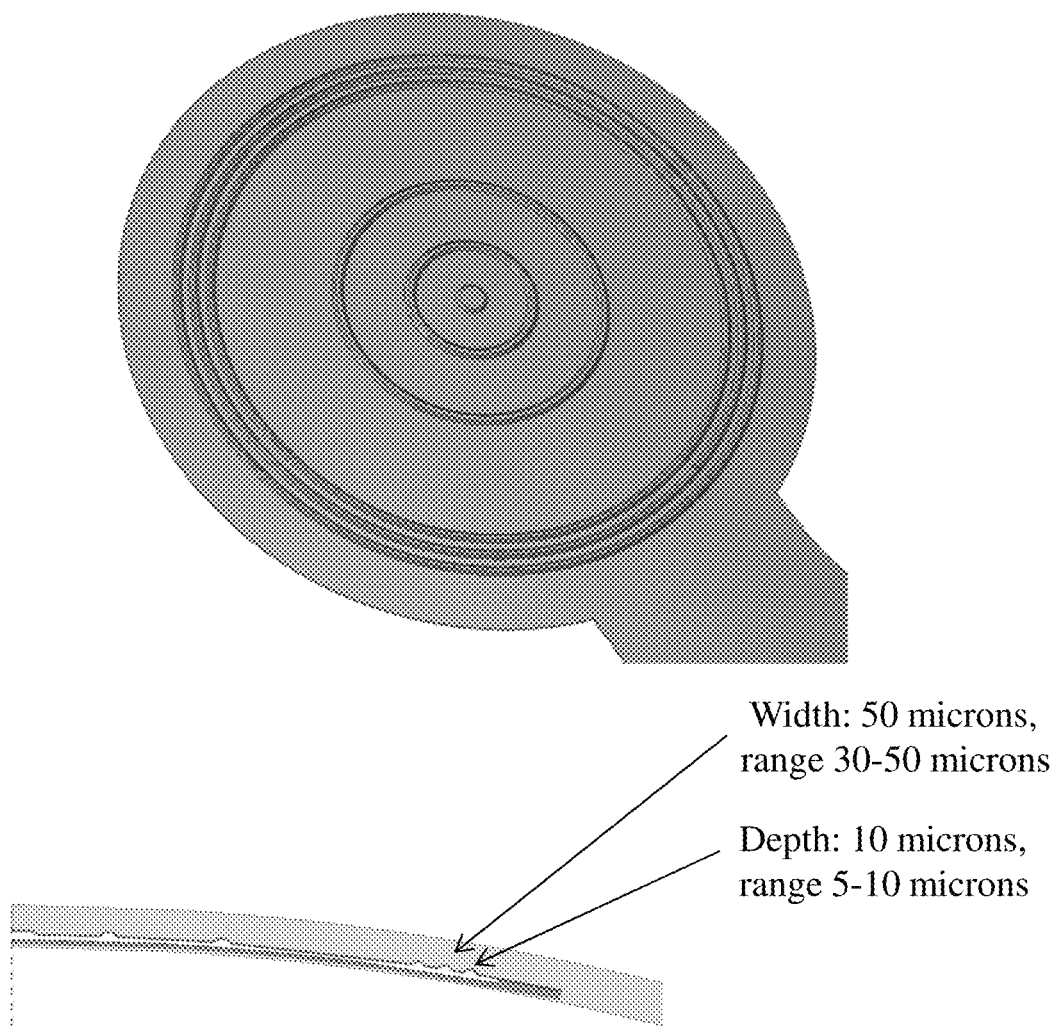
FIG. 18B shows a pattern of an accommodating contact lens membrane, in accordance with embodiments.

In some embodiments, the height and number of steps can vary across the pattern. For example, the pattern may start out with a series of one-step patterns followed by a three-step pattern, or it may comprise a series of one-step patterns, or a two-step pattern followed by a series of one-step patterns. The placement of the variable sequence of patterns may change the sag as well as the placement of steps within the pattern. FIGS. 18A and 18B and others show examples of patterned membranes with variable heights and placements.

Additional Experimental Results and Embodiments

The inventors have conducted computer modeling and clinical studies to determine structures for accommodating contact lenses that overcome deficiencies of prior accommodating contact lenses.

A preliminary estimate of increase in sag of the anterior membrane due to inflation leading to a 2.0D increase in optical power, based on calculation of increase in curvature required to effect such an increase in optical power is given in FIGS. 10 and 14. While suitable for use in accordance with embodiments, the inventors have determined that improved structures can be determined and provided.

In many embodiments, the design comprises a single, hermetically sealed fluidic module that comprises one or more separate chambers, interconnected by means of microchannels, embedded in a soft contact lens, as described herein.

The shape of the peripheral chambers are also cylindrical, and their top and bottom faces are circular or elongated, as described herein.

Figure 15:
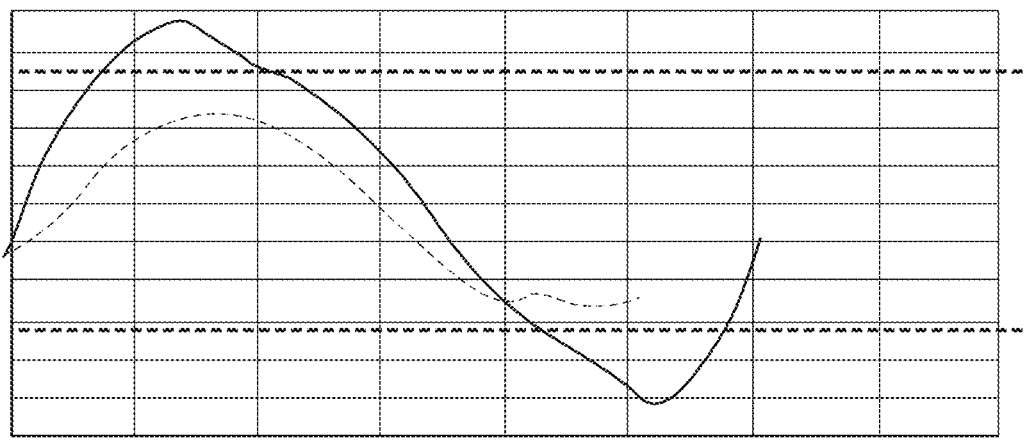
FIG. 15 shows bench test data on an accommodative soft contact lens with an embedded fluidic module, in accordance with embodiments.

These estimates were refined by performing a ray tracing analysis on Zemax, importing the data on the soft contact lens embedded with a fluidic module, results of such a simulation being shown in FIG. 15.

FIG. 15 shows a plot of increase in sag of an accommodating soft contact lens upon being compressed along the area of contact anticipated to occur with the lower eyelid.

The ray tracing analysis shows that the sag increase required ro an increase of optical power of 2.5D at the retinal plane is about 8 microns, significantly less than that estimated from expected changes in surface curvature.

The corresponding volume of fluid required to effect this compression is approximately in the range 20-30 nl.

Hydrostatic pressure simulations show that a pressure of 1000 Pa is sufficient to cause an inflation of 50 nl in a module with a central reservoir of 3.0 mm diameter (FIG. 10).

Bench tests on accommodative soft contact lenses with embedded fluidic modules show that a pressure of 1600 Pa can be required to cause an inflation of 21 microns, equivalent to an increase in surface power (measured in terms of increase in surface curvature) of 3.5D.

The data and simulation results provided herein show that a pressure of 1000 Pa or less (500-1000 Pa) can be sufficient to cause a change in optical power of 2.5D at the retinal plane, providing a fluid injection of approximately 20-30 nl into a central reservoir of diameter 3.0 mm.

This range of pressure is well within the range of pressure measured to be exerted by the power eyelid, over a contact area between the lower eyelid and the contact lens, estimated to be in the range of 0.15-5.0 sq mm, assuming a contact line having a length of 5.0 mm and a width of 0.30-1.0 mm.

The volume of fluid in the peripheral reservoirs can range from 350 nl to 800 nl, depending on the depth of the fluid in the module (range 12-30 microns).

Bench test and simulation results show that the range of lower eyelid pressures can be sufficient to eject approximately 6-25% of the total volume of fluid from the peripheral reservoirs.

In many embodiments, it is therefore helpful to reduce the volume of the peripheral chamber by approximately 30-45% in order to develop a binary response of fluid ejection of 20-30 nl corresponding to the lower end of a clinically observed eyelid pressure range.

This is accomplished by reducing the width of the peripheral reservoir, while keeping its depth constant in order to maintain engagement with the lower eyelid at down-gaze of 20 degrees.

In many embodiments, the width is reduced to 6.0-8.0 mm from the earlier value of 10.0 mm, in order to confirm the simulation results run with this smaller peripheral reservoir (corresponding to a 20-40% decrease).

FIG. 21 shows a resized peripheral reservoir for such a binary module. The peripheral reservoir has a volume in the range of 200 nl to 540 nl (370+/−170) nl, corresponding to a depth of fluid in the range of 12-30 microns.

In each of these embodiments, the lower end of the peripheral reservoir is a tangent to the line denoting the location of the lower eyelid at primary gaze, ensuring that the peripheral reservoir is not inadvertently compressed when the subject maintains a primary gaze, looking at far objects.

In many embodiments, the upper end of this volume is preferred because a greater depth of fluid prevents pooling of fluid leading to stiction at certain points on the surface of the module.

In many embodiments, the channel length is maintained at 1.0 mm, while the edge of the channel is rounded in order to avoid formation of bubbles or zones of delamination between the material of the soft contact lens and the surface of the module.

The modeling and simulation studies as described herein with reference to FIG. 15 to FIG. 24 have been performed on modules that are precurved and preshaped to form a meniscus of radius 8.4 mm, an example of the radius of curvature of the base curve of the encapsulating soft contact lens.

The radius of the curve of the module itself may be varied over a range that allows the module to fit into the contact lens body and that does not exert a significant bending stress on the soft contact lens, leading to an alteration of its base curve.

In many embodiments, for a base curve of 8.0 mm, this range of curvature of the module is within a range from about 7.5 mm to about 10.0 mm, for example.

Comparison with a target spherical shape that provides an increase of optical power of 2.50D at the center of the accommodating soft contact lens shows that the non-uniform pattern B provides a sag profile that is closer to the target sag profile.

Both patterns provide sufficient additional flexibility to the anterior membrane of the central reservoir in order to achieve the targeted increase of optical power of the contact lens, namely 2.5D at the lower end of the range of lower eyelid pressures measured clinically on early presbyopic patients.

Figure 16:
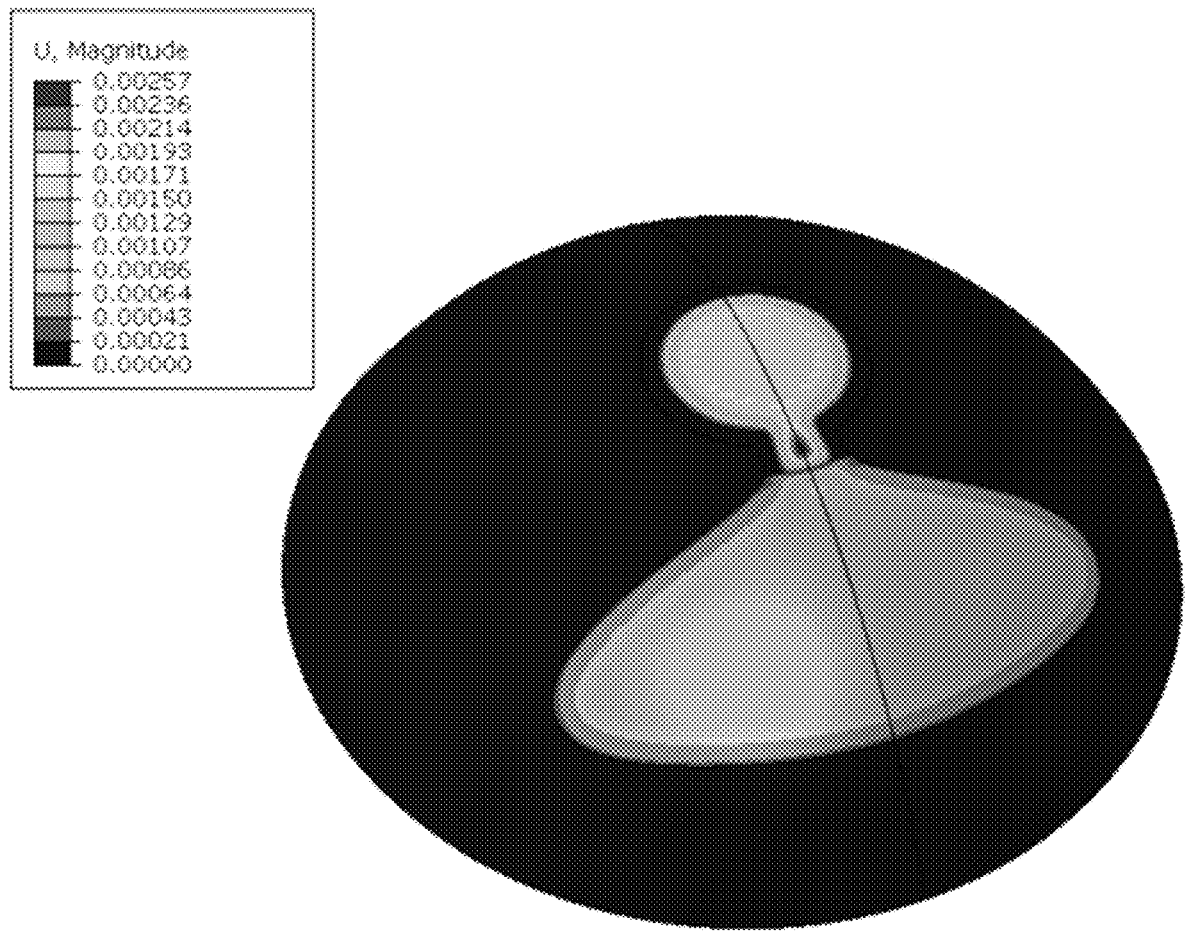
FIG. 16 shows a fluidic module embedded in a soft contact lens, in accordance with embodiments.

FIG. 15 shows bench test data on an accommodative soft contact lens with an embedded fluidic module;

FIG. 16 shows a fluidic module embedded in a soft contact lens in accordance with embodiments. Here, the color code shows the magnitude of change in sag upon application of 1000 Pa pressure;

In many embodiments, the module comprises patterning on an inner portion of the anterior membrane, for example on an outer central portion of the inner membrane. The patterning may comprise a plurality of elevated structures protruding from the anterior surface of the membrane, for example a plurality of ribs protruding from the anterior surface of the membrane. The plurality of protruding structures can be arranged in one or more of many ways, such as linear patterns, rows, or rotationally symmetric elongate protruding structures such as circular ribs.

The protruding structures can provide relative stiffness to the anterior membrane in order to shape the membrane with an optical correction profile when displaced anteriorly to provide a near vision correction, for example.

Figure 17:
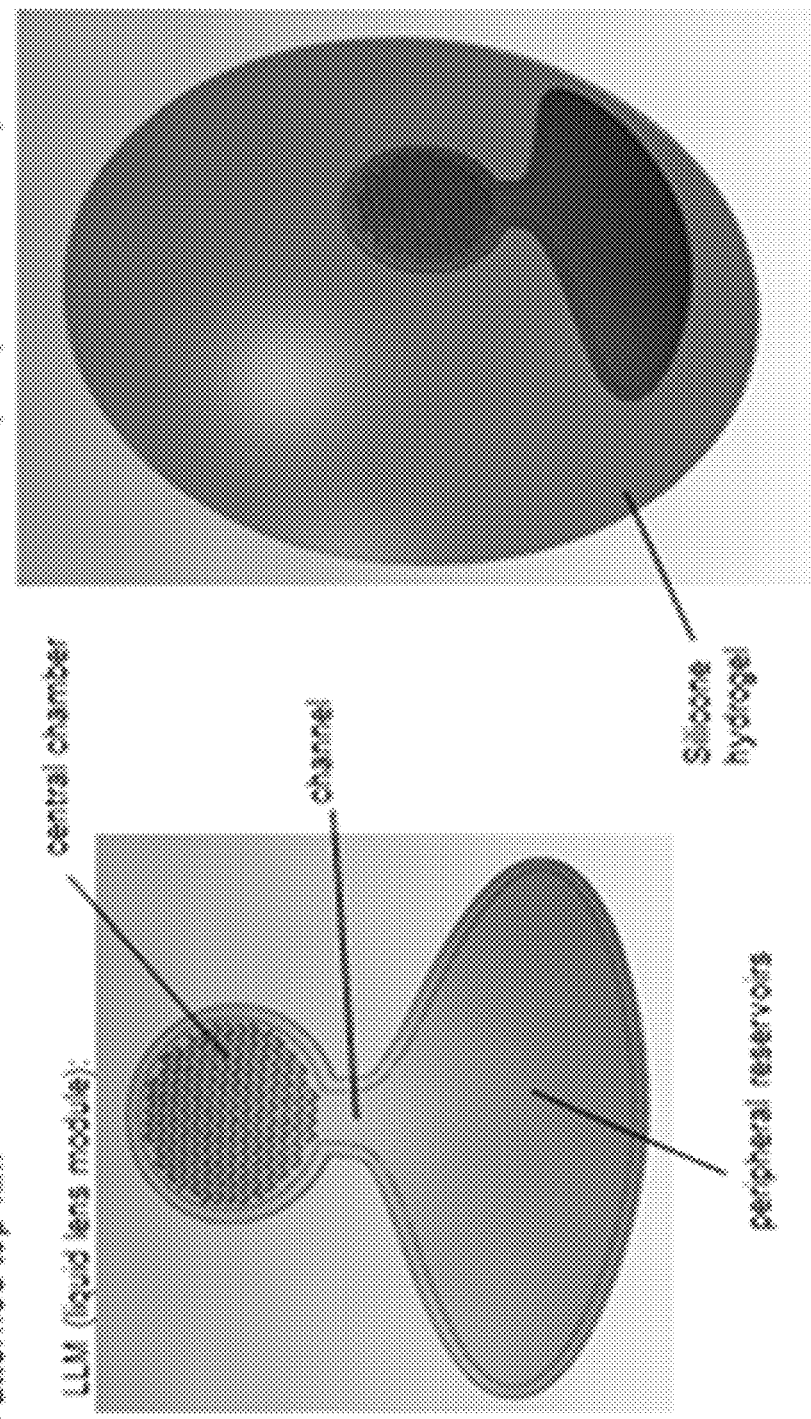
FIG. 17 shows linear chevron pattern on the central reservoir, in accordance with embodiments.

FIG. 17 shows linear chevron pattern on the central reservoir. Each row of a plurality of rows of the linear chevron pattern can extend horizontally along the optical zone of the lens when placed. The linear chevron pattern shows an example of a pattern on the central optical module as described herein.

FIG. 18A shows a pattern (Pattern A) of an accommodating contact lens membrane, in accordance with embodiments. The pattern may comprise a rotationally symmetric pattern distributed about a central axis of the central membrane. The spacing between each elevation of the central pattern can vary to produce a desired optical lens having decreased aberrations, for example. The spacing between each of the protruding rib structures can be within a range from about 30 to about 50 um, for example. The depth of each of the channels that defines the protruding structures can be within a range from about 5 to 10 um, for example.

FIG. 18B shows a pattern (Pattern B) of an accommodating contact lens membrane, in accordance with embodiments. The patterning can be configured in one or more of many ways to provide a desired optical correction. For example, the inner portion may comprise an inner plurality of protruding circular structures, and the outer portion may comprise an outer plurality of protruding circular structures, in which the outer protruding structures are spaced closer together than the inner protruding circular structures. An intermediate portion of the anterior membrane located radially between the inner circular structures and the outer circular structures may comprise fewer circular structures than the inner and outer portions, for example.

Figure 19:
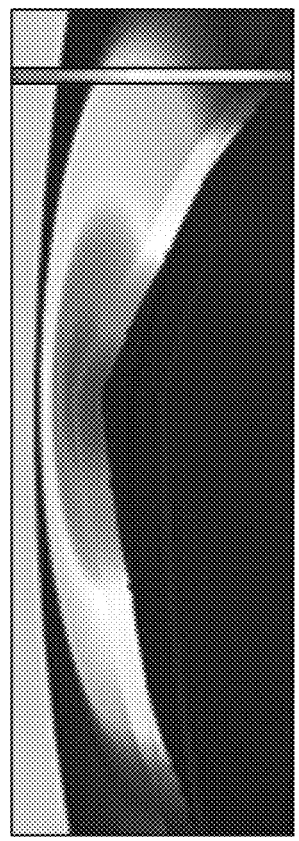
FIG. 19 shows simulation of inflation of the central reservoir comprising Patterns A and B of FIGS. 18A and 18B, respectively, in accordance with embodiments.
Figure 19:
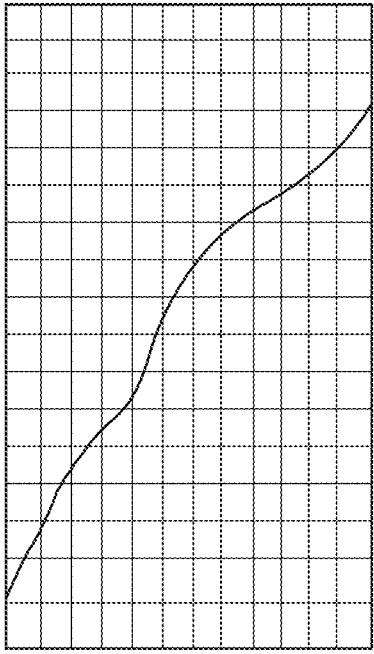
Figure 19:
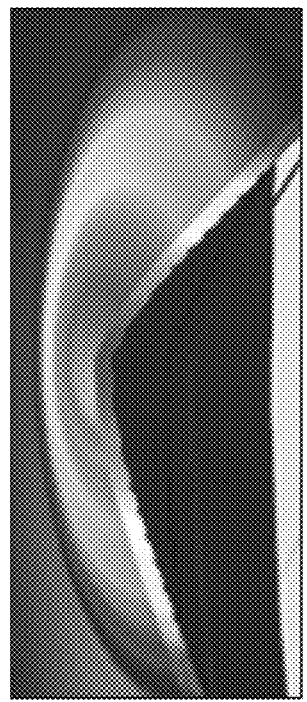
Figure 19:
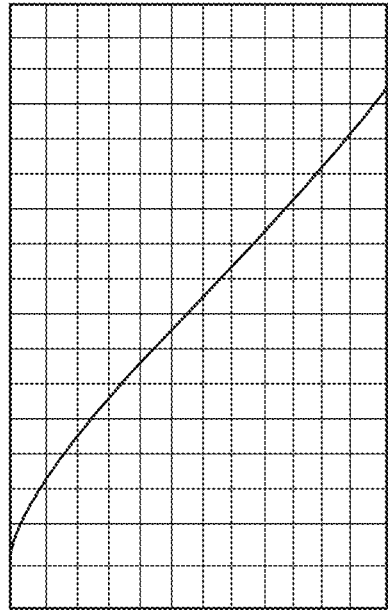

FIG. 19 shows simulation of inflation of the central reservoir decorated with Patterns A and B of FIGS. 18A and 18B, respectively. Different pressures were used in each case, 200 Pa for pattern A and 430 Pa for pattern B, in accordance with embodiments. These figures show that the patterning can provide a smoother surface, or a best fit to a target surface. The 6.1 um sag height can be capable of providing a near vision correction as described herein, with volumes of 15 nL and 18 nL, respectively for patterns A and B, for example.

Figure 20:
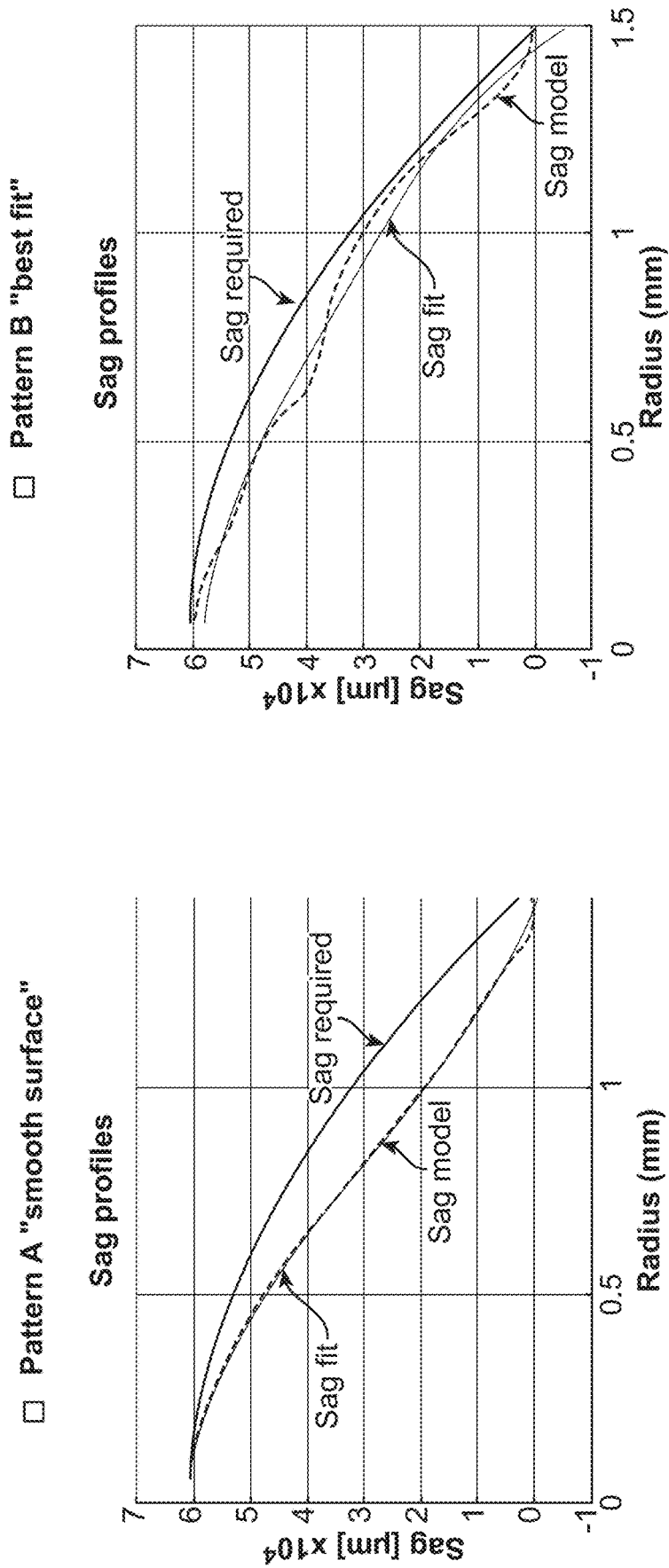
FIG. 20 shows comparison of the anterior membrane geometry of the central reservoir to a target spherical shape required for a 2.5D increase in optical power at the central optical zone of the accommodative contact lens, in accordance with embodiments.

FIG. 20 shows comparison of the anterior membrane geometry of the central reservoir to a target spherical shape to provide a 2.5D increase in optical power at the central optical zone of the accommodative contact lens, in accordance with embodiments. The 2.5D optical power can be provided with a 6 um sag height as described herein.

Figure 21A:
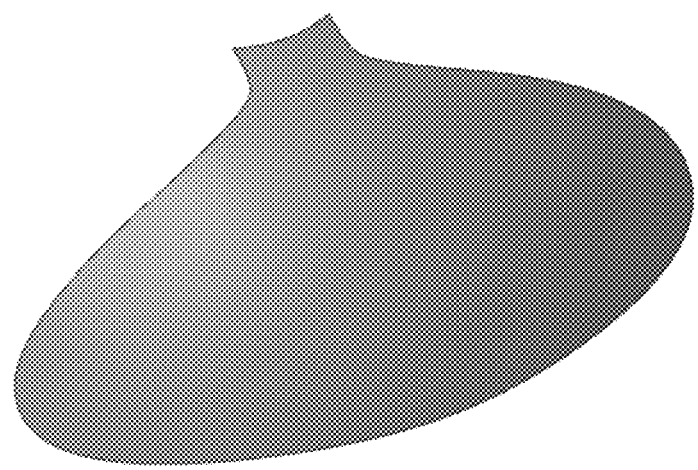
FIGS. 21A and 21B shows CAD models of resized peripheral reservoirs, in accordance with embodiments.
Figure 21B:
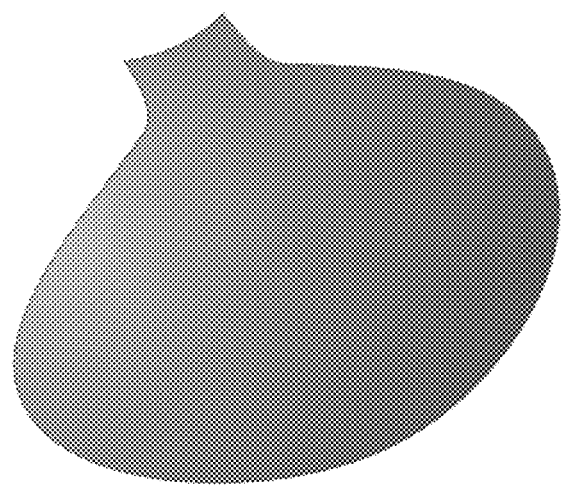

FIGS. 21A and 21B shows CAD models of resized peripheral reservoirs, in accordance with embodiments. FIG. 21A shows an outer (peripheral) reservoir having a maximum dimension across of about 8 mm. FIG. 21B shows the outer (peripheral) reservoir having a maximum dimension across of about 6 mm. The 6 mm reservoir can be combined with binary embodiments as described herein and can contain a decreased amount of fluid to inhibit variability among users.

Figure 22A:
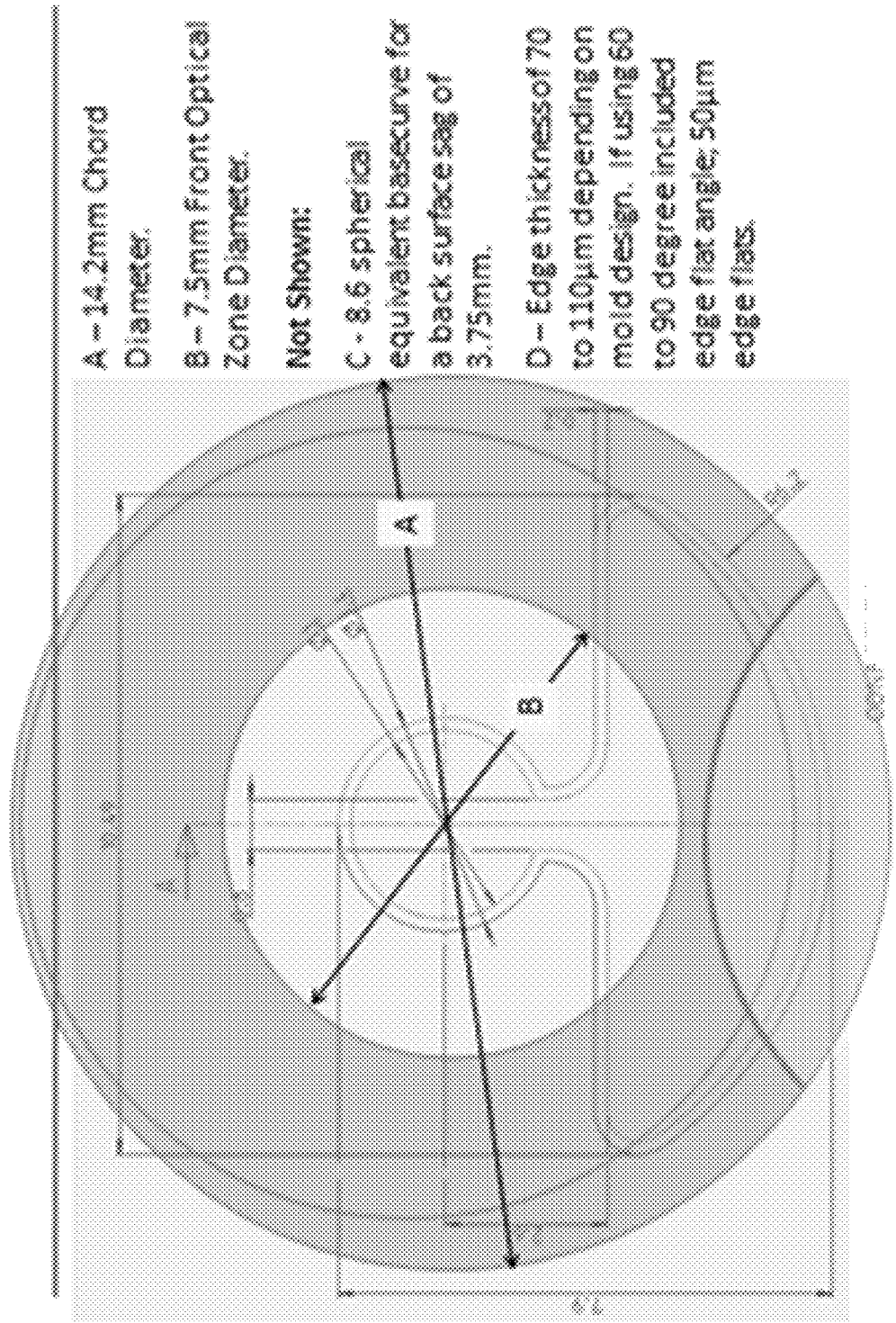
FIG. 22A shows a fluidic module embedded in a soft contact lens, in accordance with embodiments.

FIG. 22A shows a fluidic module embedded in a soft contact lens as described herein. The module comprises a fluidic module that may be embedded into a soft contact lens for correction of presbyopia as described herein, for example with a meniscus shaped inner (central) optical reservoir and an outer (peripheral) reservoir. In many embodiments, the contact lens comprises a single, hermetically sealed fluidic module that comprises one or more separate chambers, interconnected with channels such as micro-channels, embedded in a soft contact lens.

In many embodiments, the soft contact lens comprises a chord length (Dimension A) within a range from about 12-15 mm, for example about 14 mm. In many embodiments, the soft contact lens comprises an optical zone having a diameter (Dimension B) sized to correct refractive error of the eye such as one or more of nearsightedness, far sightedness, or astigmatism. In many embodiments, the accommodating contact lens comprises a base curve on the posterior surface sized to fit the cornea of the eye (Dimension C). The base curve can be about 8.6 mm, for example, and can be sized based on corneal topography measurements. In many embodiments, the soft contact lens material located on the posterior (lower) surface of the contact lens defines the base curvature of the contact lens. In many embodiments, the self-supporting module as described herein embedded in the soft contact lens material comprises a lower surface having a base curvature corresponding to the base curvature of the contact lens, in order to decrease the thickness of the contact lens. The inner (central) optical reservoir and outer (peripheral) reservoir may each comprise upper and lower curved surfaces having a curvatures corresponding to the base curve of the contact lens in order to provide meniscus shaped reservoirs sized to fit between the upper and lower surface of the contact lens.

In many embodiments, the contact lens comprises an edge thickness within a range from about 50 um to about 110 um, for example, such as within a range from about 60 um to about 110 um.

FIG. 22B shows example specifications of the fluidic module as described herein, in accordance with embodiments. In many embodiments, the inner (central) reservoir comprises a diameter within a range from about 2.5 to about 3.5 mm, for example. The channel extending between the inner (central) optical reservoir chamber and the outer (peripheral) reservoir chamber can be within a range from about 0.5 to about 1.5 mm, for example. The channel may comprise a cross sectional thickness within a range from about 10 um to about 30 um, for example, and a cross-sectional width within a range from about 500 um to about 1100 um. The thickness of the anterior membrane of the module can be within a range from about 2 to 10 um, for example about 5 um. The thickness of the posterior membrane of the module can be within a range from about 10 um to about 40 um, for example about 25 um. Each of the anterior membrane and the posterior membrane may have similar spherical curvatures in order to provide the meniscus shape as described herein.

Figure 23:
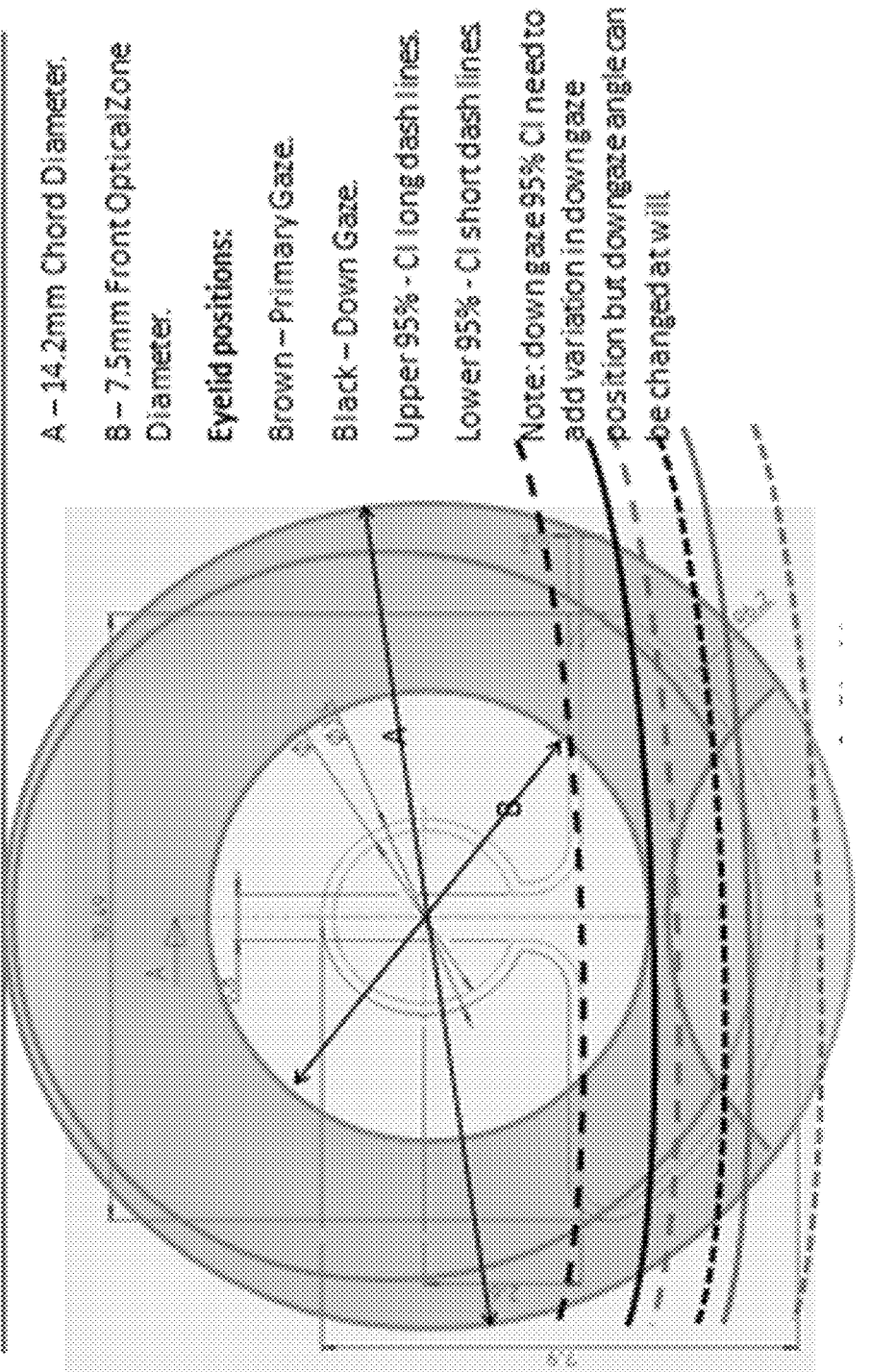
FIG. 23 shows variations in eyelid position with respect to an accommodating contact lens for primary (far vision) gaze and downward gaze, in relation to 95% confidence intervals for a patient population, in accordance with embodiments.

FIG. 23 shows variations in eyelid position with respect to an accommodating contact lens for primary (far vision) gaze and downward gaze, in relation to 95% confidence intervals for a patient population, in accordance with embodiments. The range of location of the lower eyelid relative to the soft contact lens upon down gaze. The brown (lighter) lines represent the range of locations of the lower eyelid during primary gaze and the black (darker) lines represent the lower eyelid positions during down-gaze (95%). In many embodiments, the outer (peripheral) module is positioned such that the lower eyelid, the upper edge of which is represented by the lower dotted black line, has substantial overlap with the peripheral reservoir.

In many embodiments, the fluidic module is located inside the soft contact lens such that the geometrical center of the contact lens anterior surface optic is co-linear with the geometrical center of the central chamber of the fluidic module.

In many embodiments, the fluidic module is positioned in the contact lens such that the peripheral reservoir is optimally located to engage the lower eyelid at down-gaze as shown in FIG. 23.

Figure 24:
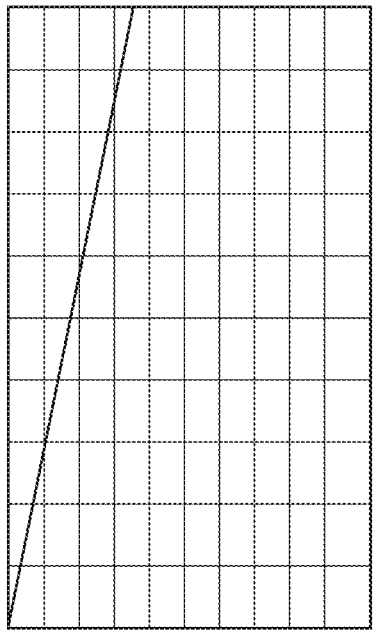
FIG. 24 shows ray tracing analysis showing that the sag increase required Ro an increase of optical power of 2.5D at the retinal plane is about 8 microns, in accordance with embodiments.
Figure 24:
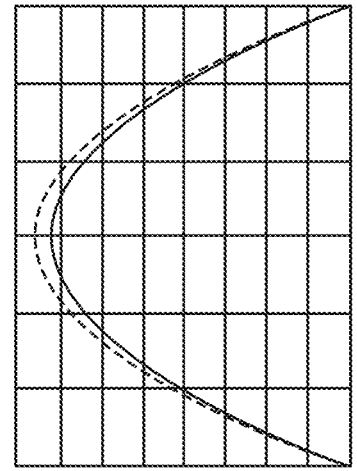

FIG. 24 shows ray tracing analysis showing that the sag increase to provide Ro (central curvature) with an increase of optical power of 2.5D at the retinal plane is about 8 microns, significantly less than that estimated from expected changes in surface curvature; the volume of fluid required to cause this inflation is correspondingly less, approximately 21 nl, as compared to 50 nl for a 2.0D increase in surface power for a similar diameter of optical correction, in accordance with embodiments.

In many embodiments, the apsheric profile comprises a central curvature (Ro), and a conic constant. The central curvature of Ro corresponds to the central optical correction of the patient and the conic constant is dimensioned to provide an aspheric profile to the optically corrective surface for near vision correction. In many embodiments, the central curvature and conic constant of the aspheric optical surface profile are arranged to provide near vision optical correction to an eye comprising at least some aberration.

In many embodiments, the inner (central) optical zone comprises a near vision shape profile to correct aberrations of the eye. In many embodiments, the inner (central) optical zone comprises a shape profile to provide near vision in combination with one or more aberrations of the eye such as one or more of spherical aberration, coma, trefoil, fourth order spherical aberration, sixth order spherical aberration, or one or more aberrations measured with a wavefront sensor.

In many embodiments, a model eye corresponding to a population of patients can be modeled, and the shape profile of the anterior membrane of the inner (central) lens configured to provide near vision for an eye having aberrations corresponding to values of a population of patients. While the aberrations can be modeled in one or more of many ways, in many embodiments, the optical properties of the eye are determined with ray tracing, and the anterior membrane configured to provide near vision based on the ray tracing. The shape profile of the near vision lens may comprise an optically corrective aspheric profile to correct aberrations of the eye, for example.

In many embodiments, the anterior membrane of the inner (central) reservoir comprises a varying thickness profile. In many embodiments, the anterior membrane comprise a varying thickness profile with a plurality of protrusions to provide the aspheric shape. Alternatively or in combination, the thickness profile of the anterior membrane can vary with smoothly or with steps, for example, in order to provide the aspheric shape profile to provide near vision to the user.

The decreased amount of fluid to provide the optical correction can be used to design the module with decreased fluidic movement.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An accommodating contact lens comprising:
a central optical reservoir comprising an anterior membrane and a posterior membrane, wherein the anterior membrane comprises a variable thickness profile to decrease aberrations; and
an outer reservoir fluidically coupled to the central optical reservoir with a channel;
wherein the central optical reservoir comprises an aspheric near vision shape profile, the near vision aspheric shape profile comprising a change in volume when transitioning from a far vision shape profile to the near vision profile and wherein the change in volume comprises less than a volume of a spherical profile of similar diameter transitioning from a far vision shape profile to a near vision profile.

2. The accommodating contact lens of claim 1, further comprising a soft contact lens material disposed over the anterior membrane and wherein an index of refraction of the soft contact lens material approximates an index of refraction of the anterior membrane in order to inhibit optical effects of the variable thickness profile of the anterior membrane.

3. The accommodating contact lens of claim 2, wherein the plurality of protrusions is arranged to provide an aspheric surface to provide near vision to the user.

4. The accommodating contact lens of claim 3, wherein the plurality of protrusions comprises a first plurality of inner protrusions having first spacings between said inner protrusions and a second plurality of outer protrusions having second spacings between said second protrusions, said first spacings different from said second spacings to inhibit aberrations.

5. The accommodating contact lens of claim 4 wherein said second spacings comprise amounts greater than said first spacings.

6. The accommodating contact lens of claim 2, wherein the plurality of protrusions comprises variable spacing among each of the plurality of protrusions to inhibit the aberrations.

7. The accommodating contact lens of claim 3, wherein the plurality of protrusions comprises one or more of steps or ribs.

8. The accommodating contact lens of claim 3, wherein the plurality of protrusions comprises concentric protrusions arranged about a central axis of the central optical reservoir.

9. The accommodating contact lens of claim 3, wherein the plurality of protrusions comprises varied heights.

10. The accommodating contact lens of claim 1, wherein the variable thickness profile comprises a plurality of protrusions arranged to inhibit aberrations.

11. The accommodating contact lens of claim 1, wherein the variable thickness profile comprises a continuous profile of varying thickness or an incrementally stepped profile of varying thickness to inhibit aberrations.

12. The accommodating contact lens of claim 1, wherein one or more of the posterior membrane or the anterior membrane comprises a curved spherical in order to provide far vision correction to the user in combination with an anterior surface of the contact lens defining an optical zone.

13. The accommodating contact lens of claim 1, wherein the posterior membrane and the anterior membrane each comprises a curved spherical surface defining a meniscus profile of the central optical reservoir in order to provide far vision correction to the user in combination with an anterior surface of the contact lens defining an optical zone.

14. The accommodating contact lens of claim 1, wherein the anterior membrane comprises an aspheric profile when providing a near vision correction to the user.

15. The accommodating contact lens of claim 1, wherein a soft contact lens material comprises a thickness extending between an anterior optical surface of the contact lens and an anterior surface of the anterior membrane and wherein the thickness varies across the anterior membrane in order to correct vision of the user.

16. The accommodating contact lens of claim 1, wherein a soft contact lens material comprises a thickness extending between an anterior optical surface of the contact lens and an anterior surface of the anterior membrane and wherein the thickness varies across the anterior membrane in order to inhibit optical artifacts related to variations in thickness of the anterior membrane.

17. The accommodating contact lens of claim 1, wherein the outer reservoir comprises an upper boundary positioned so as to correspond to an upper position of a lower lid of the eye for an upper normal bound of a 95% confidence interval of a patient population and a lower boundary positioned to overlap substantially with the lower lid of the eye for a lower normal bound of the 95% confidence interval of the patient population.

\* \* \* \* \*